US012619150B2

(12) United States Patent
Kori et al.

(10) Patent No.: US 12,619,150 B2
(45) Date of Patent: May 5, 2026

(54) MATERIAL FOR FORMING ORGANIC FILM, SUBSTRATE FOR MANUFACTURING SEMICONDUCTOR DEVICE, METHOD FOR FORMING ORGANIC FILM, PATTERNING PROCESS, AND COMPOUND FOR FORMING ORGANIC FILM

(71) Applicant: SHIN-ETSU CHEMICAL CO., LTD., Tokyo (JP)

(72) Inventors: Daisuke Kori, Joetsu (JP); Takashi Sawamura, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 1144 days.

(21) Appl. No.: 17/578,624

(22) Filed: Jan. 19, 2022

(65) Prior Publication Data

US 2022/0269175 A1 Aug. 25, 2022

(30) Foreign Application Priority Data

Feb. 15, 2021 (JP) .................................. 2021-21724

(51) Int. Cl.

| | |
|---|---|
| ***C07D 319/14*** | (2006.01) |
| ***C07D 319/24*** | (2006.01) |
| ***C09D 171/12*** | (2006.01) |
| ***G03F 7/09*** | (2006.01) |
| ***G03F 7/11*** | (2006.01) |
| ***H10P 76/20*** | (2026.01) |
| ***H10P 76/40*** | (2026.01) |

(52) U.S. Cl.

CPC .............. *G03F 7/11* (2013.01); *C07D 319/14* (2013.01); *C07D 319/24* (2013.01); *C09D 171/12* (2013.01); *G03F 7/094* (2013.01); *H10P 76/2043* (2026.01); *H10P 76/405* (2026.01); *H10P 76/4083* (2026.01); *H10P 76/4085* (2026.01); *H10P 76/4088* (2026.01)

(58) Field of Classification Search

CPC ............................ C07D 319/14; C07D 319/24

See application file for complete search history.

(56) References Cited

U.S. PATENT DOCUMENTS

| | | | |
|---|---|---|---|
| 6,121,495 | A | 9/2000 | Babb et al. |
| 2002/0106909 | A1 | 8/2002 | Kato et al. |
| 2005/0255712 | A1 | 11/2005 | Kato et al. |
| 2006/0019195 | A1 | 1/2006 | Hatakeyama et al. |
| 2006/0204891 | A1 | 9/2006 | Hatakeyama |
| 2009/0221779 | A1 | 9/2009 | Kubo et al. |
| 2009/0274978 | A1 | 11/2009 | Ohashi et al. |
| 2010/0099044 | A1 | 4/2010 | Hatakeyama et al. |
| 2012/0252217 | A1 | 10/2012 | Minegishi et al. |
| 2013/0302990 | A1 | 11/2013 | Watanabe et al. |
| 2016/0085152 | A1 | 3/2016 | Nakafuji et al. |
| 2017/0009006 | A1 | 1/2017 | Ding et al. |
| 2017/0184968 | A1 | 6/2017 | Kori et al. |
| 2018/0158674 | A1 | 6/2018 | Yamada et al. |

FOREIGN PATENT DOCUMENTS

| | | | |
|---|---|---|---|
| JP | H11-512430 | A | 3/1997 |
| JP | 2002-334869 | A | 11/2002 |
| JP | 2005-041938 | A | 2/2005 |
| JP | 2005-128509 | A | 5/2005 |
| JP | 2006-285095 | A | 10/2006 |
| JP | 2006-293298 | A | 10/2006 |
| JP | 2007-199653 | A | 8/2007 |
| JP | 2009-206447 | A | 9/2009 |
| JP | 2009-269953 | A | 11/2009 |
| JP | 2010-122656 | A | 6/2010 |

(Continued)

OTHER PUBLICATIONS

Jul. 19, 2022 Extended European Search Report issued in European Application No. 22155688.9.

(Continued)

*Primary Examiner* — Adam C Milligan
*Assistant Examiner* — Karen Cheng
(74) *Attorney, Agent, or Firm* — OLIFF PLC.

(57) ABSTRACT

The present invention is a material for forming an organic film, containing: (A) a compound for forming an organic film shown by the following general formula (1A); and (B) an organic solvent, where $W_1$ represents a tetravalent or hexavalent organic group, n1 represents an integer of 1 or 2, n2 represents 2 or 3, each $R_1$ independently represents any in the following formula (1B), and a hydrogen atom of a benzene ring in the formula (1A) is optionally substituted with a fluorine atom. This provides: a compound having a dioxin structure, which is cured even under film formation conditions in inert gas, and which is capable of forming an organic underlayer film having not only excellent heat resistance and properties of filling and planarizing a pattern formed on a substrate, but also favorable film formability and adhesiveness to a substrate; and an organic film material containing the compound.

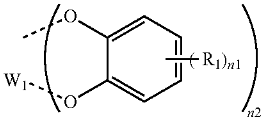

(1A)

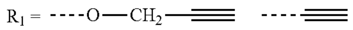

(1B)

23 Claims, 4 Drawing Sheets

(56) References Cited

FOREIGN PATENT DOCUMENTS

| | | | |
|---|---|---|---|
| JP | 2010-181605 | A | 8/2010 |
| JP | 2012-215842 | A | 11/2012 |
| JP | 2013-253227 | A | 12/2013 |
| JP | 2016-044272 | A | 4/2016 |
| JP | 2016-060886 | A | 4/2016 |
| JP | 2017-014193 | A | 1/2017 |
| JP | 2017-119671 | A | 7/2017 |
| JP | 2018-092170 | A | 6/2018 |
| WO | 2004/066377 | A1 | 8/2004 |
| WO | 2014/208324 | A1 | 12/2014 |
| WO | 2016/047924 | A2 | 3/2016 |

OTHER PUBLICATIONS

Klyatskaya, Svetlana V. et al: "Synthesis and chemical properties of polyacetylenic derivatives of benzo- and dibenzo- crown ethers", ARKIVOC, vol. 2003, No. 13, Jun. 6, 2003 (Jun. 6, 2003), pp. 21-34, XP055938888.

Yu, Xianglin et al: "Tetraazatetraoxodecacene and tetraazatetrathiodecacene: Synthesis, crystal structures, linear and third-order nonlinear optical properties", Dyes and Pigments, Elsevier Applied Science Publishers Barking, GB, vol. 161, Jul. 21, 2018 (Jul. 21, 2018), pp. 130-136, XP085510911.

[FIG. 1]
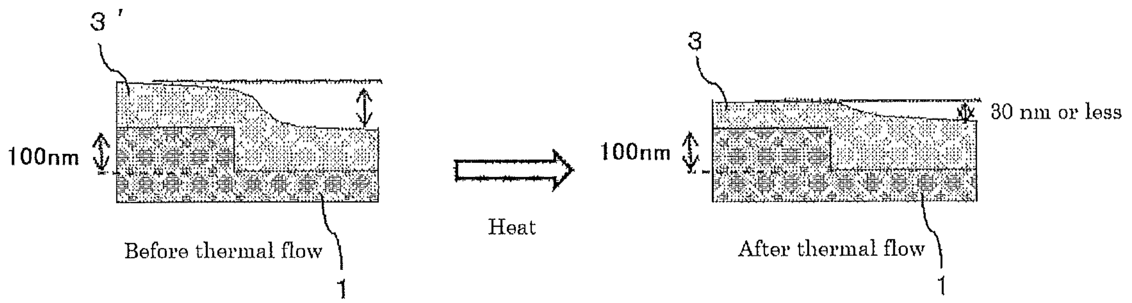
[FIG. 2]
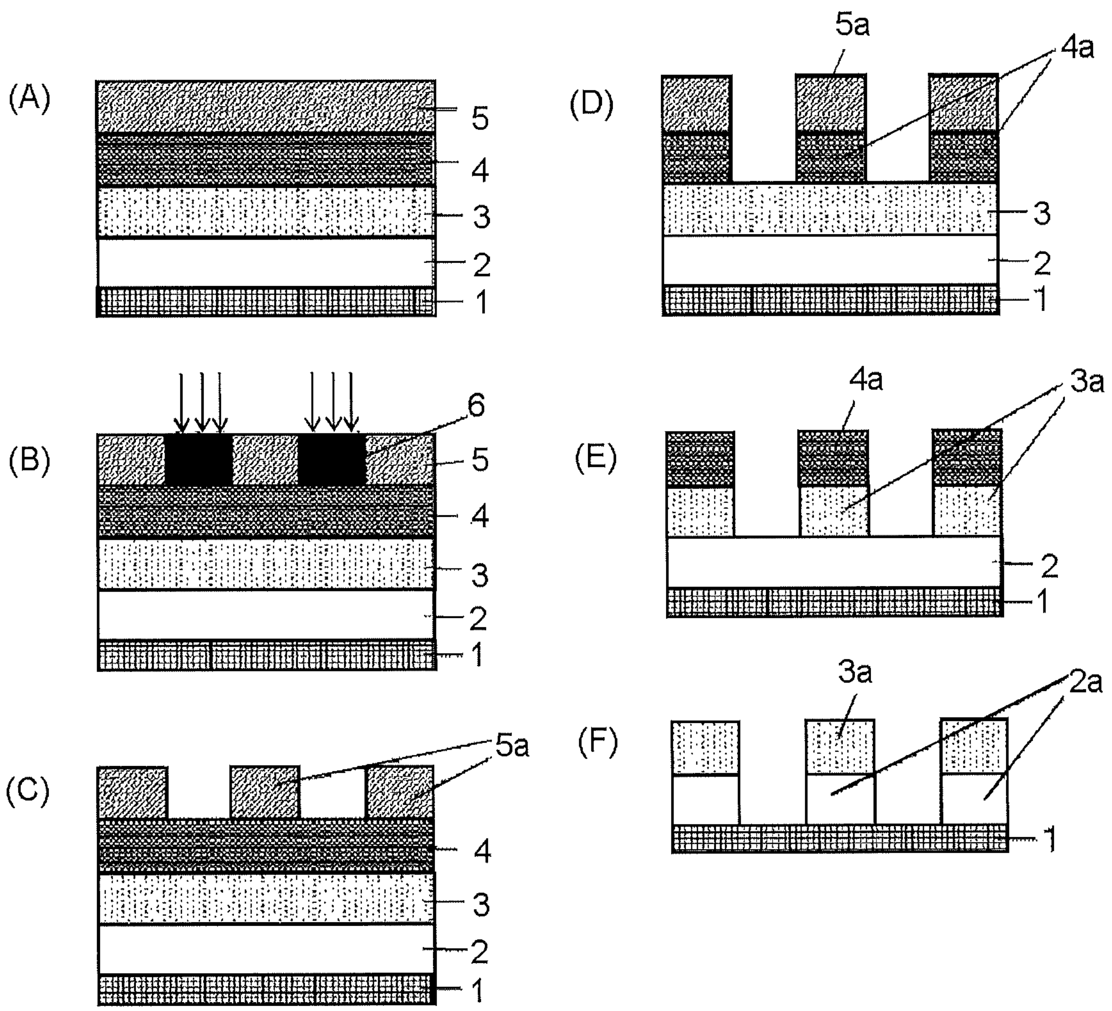

[FIG. 3]
(G)
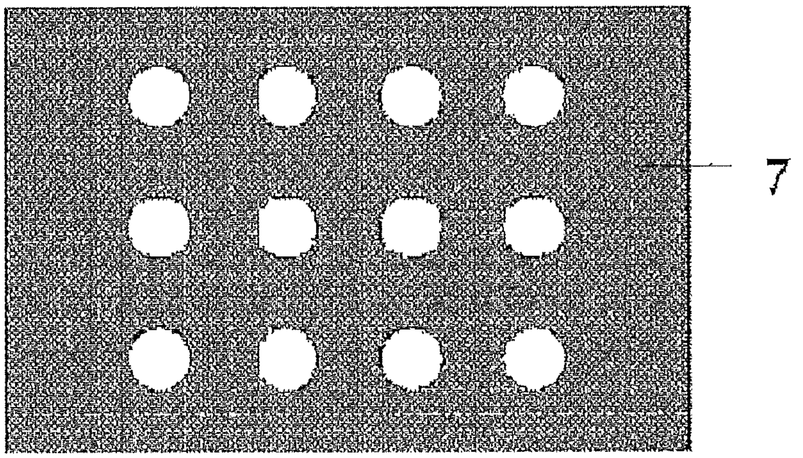
(H)
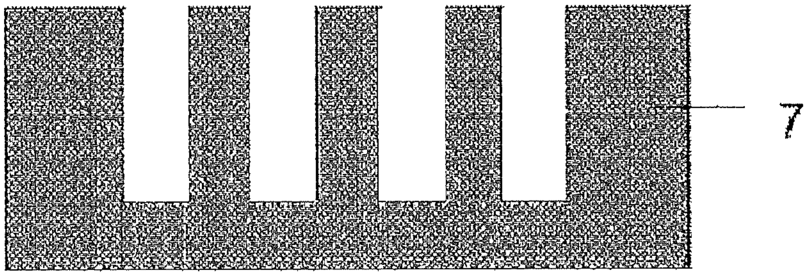
(I)
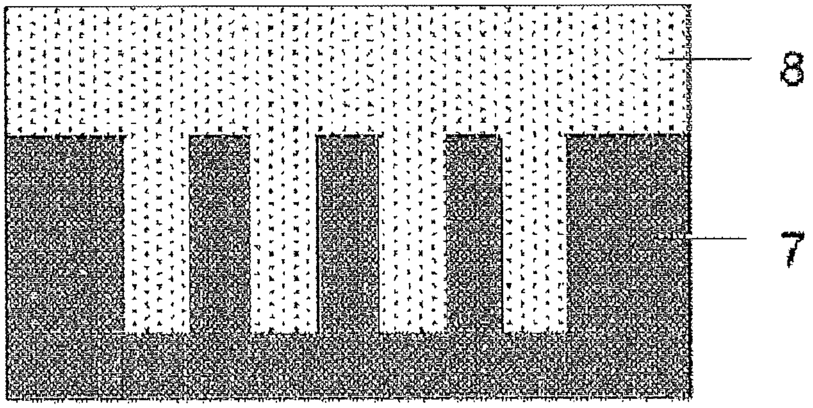

[FIG. 4]
(J)
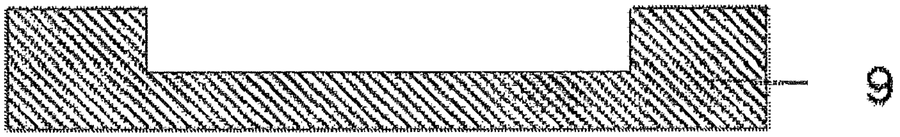
(K)
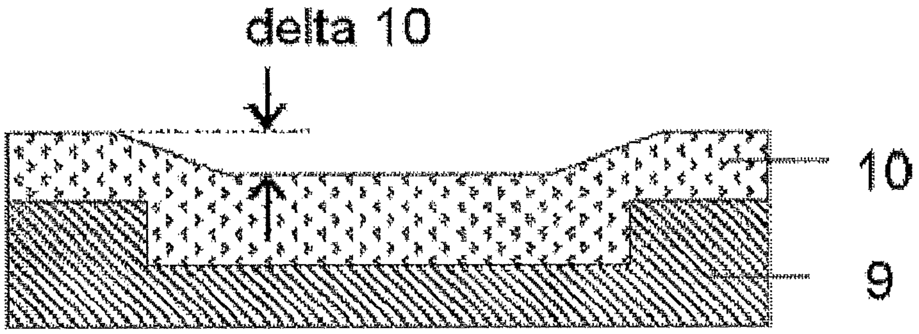

[FIG. 5]
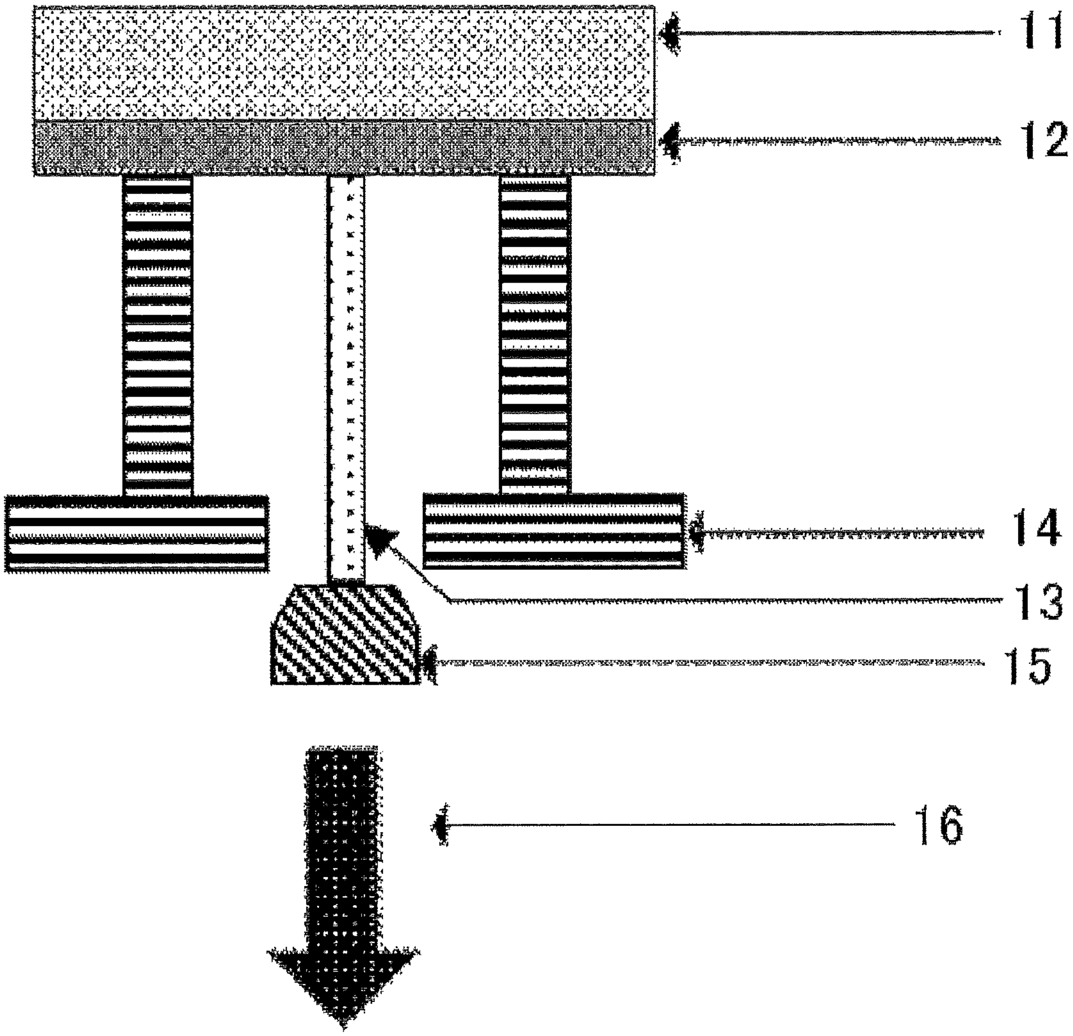

MATERIAL FOR FORMING ORGANIC FILM, SUBSTRATE FOR MANUFACTURING SEMICONDUCTOR DEVICE, METHOD FOR FORMING ORGANIC FILM, PATTERNING PROCESS, AND COMPOUND FOR FORMING ORGANIC FILM

TECHNICAL FIELD

The present invention relates to: a material for forming an organic film used in a semiconductor device manufacturing process; a substrate for manufacturing a semiconductor device by using the material; a method for forming an organic film using the material; a patterning process according to a multilayer resist method using the material; and a compound for forming an organic film suitably used in the material.

BACKGROUND ART

Conventionally, high integration and high processing speed of semiconductor devices have been achieved through the miniaturization of pattern size by shortening the wavelength of light sources in lithography technology using light exposure (photolithography), which is commonly employed technology. To form such a fine circuit pattern on a substrate for a semiconductor device (substrate to be processed), the following method is generally employed in which the substrate to be processed is processed by dry-etching while using a patterned photoresist film as an etching mask. In practice, however, there is no dry-etching method capable of providing an absolute etching selectivity between the photoresist film and the substrate to be processed. Hence, recently, it has been common to process a substrate by a multilayer resist method. This method is as follows: first, an underlayer film having an etching selectivity different from that of a photoresist film (hereinafter, resist upper layer film) is placed between the resist upper layer film and a substrate to be processed; a pattern is formed in the resist upper layer film; then, the pattern is transferred to the underlayer film by dry-etching while using the resist upper layer film pattern as a dry-etching mask; furthermore, the pattern is transferred to the substrate to be processed by dry-etching while using the underlayer film as a dry-etching mask.

One of the multilayer resist methods is a 3-layer resist method which can be performed with a typical resist composition used in a monolayer resist method. In this three-layer resist method, a substrate to be processed is coated with an organic underlayer film material composed of an organic resin-containing composition and then baked to form an organic underlayer film (hereinafter, organic film); the organic film is subsequently coated with a resist middle layer film material composed of a composition containing a silicon-containing resin, and baked to form a silicon-containing film (hereinafter, silicon-containing resist middle layer film); thereafter, a typical organic photoresist film (hereinafter, resist upper layer film) is formed on the silicon-containing resist middle layer film. The resist upper layer film is patterned and then subjected to dry-etching with fluorine-based gas plasma, so that the resist upper layer film pattern can be transferred to the silicon-containing resist middle layer film. This is because the organic resist upper layer film can exhibit a favorable etching selectivity ratio relative to the silicon-containing resist middle layer film. This method allows a pattern to be easily transferred to the silicon-containing resist middle layer film even if the resist upper layer film does not have sufficient film thickness for directly processing the substrate to be processed or if the resist upper layer film does not have sufficient dry-etching resistance for processing the substrate to be processed. This is because the silicon-containing resist middle layer film generally has a film thickness equal to or smaller than that of the resist upper layer film. Subsequently, while using the silicon-containing resist middle layer film having the transferred pattern as a dry-etching mask, the pattern is transferred to the organic film by dry-etching with oxygen- or hydrogen-based gas plasma. Thereby, the pattern can be transferred to the organic film having dry-etching resistance sufficient for substrate processing. This organic film pattern having the transferred pattern can be transferred to the substrate by dry-etching with a fluorine-based gas, chlorine-based gas, or the like.

Meanwhile, the miniaturization in the semiconductor device manufacturing process is approaching the limit inherent in the wavelength of light sources for photolithography. Accordingly, recently, the high integration of semiconductor devices that does not rely on miniaturization has been examined. As one means for the high integration, semiconductor devices having complicated structures such as multigate structures have been examined, and some of these have already been put into practical use. In forming such structures by multilayer resist methods, it is possible to employ an organic film material which is capable of filling a fine pattern including hole, trench, and fin formed on a substrate to be processed with a film without void, and capable of filling a step- or pattern-dense region and a pattern-free region with a film to planarize the regions. The use of such an organic film material to form an organic film having a flat surface on a stepped substrate can reduce fluctuations in film thicknesses of a silicon-containing resist middle layer film and a resist upper layer film formed thereon, and can suppress reductions in a focus margin in photolithography and a margin in a subsequent step of processing the substrate to be processed. This makes it possible to manufacture semiconductor devices with high yields. On the other hand, in the monolayer resist method, the upper resist film has to have a large film thickness to fill a stepped or patterned substrate to be processed. As a result, for example, pattern collapse occurs after exposure and development, and the pattern profile deteriorates due to reflection from the substrate at exposure. Consequently, the pattern formation margin at exposure is narrowed, making it difficult to manufacture semiconductor devices with high yields.

Furthermore, as techniques for the high processing speed of next-generation semiconductor devices, for example, the application of the following materials have also started to be examined: novel materials having high electron mobility using strained silicon, gallium arsenic, and so forth; and high-precision materials such as ultrathin polysilicon controlled in units of angstrom. However, in substrates to be processed to which such novel high-precision materials are applied, the materials of the substrates to be processed may be corroded by oxygen in air under conditions during the planarization film formation from an organic film material as described above, for example, film formation conditions of air and 300° C. or higher. Hence, such a performance as a high processing speed of a semiconductor device according to the material design cannot be exhibited, and industrially satisfactory yield may not be achieved. For this reason, an organic film material capable of forming a film in an inert gas has been desired so as to avoid a decrease in yield due to substrate corrosion by air under such high temperature conditions.

Conventionally, condensed resins using aromatic alcohols and carbonyl compounds such as ketones and aldehydes as condensing agents for a phenol-based compound or naphthol-based compound have been known as materials for forming an organic film for multilayer resist methods. Examples of such condensed resins include a fluorene bisphenol novolak resin described in Patent Document 1, a bisphenol compound and a novolak resin thereof described in Patent Document 2, a novolak resin of an adamantane phenol compound described in Patent Document 3, a bis-naphthol compound and a novolak resin thereof described in Patent Document 4, and the like. Crosslinking using a methylol compound as a crosslinking agent, or a curing action by a crosslinking reaction through oxidation at the α-position of an aromatic ring due to the action of oxygen in air and the subsequent condensation, causes such a material to form a film having solvent resistance in relation to a coating film material used in the subsequent step.

Furthermore, an organic film material in which triple bonds are employed as intermolecular crosslinking groups in a curable resin is known. For example, Patent Documents 5 to 15, etc. are known. In these materials, a cured film having solvent resistance is formed not only by the methylol-involving crosslinking, but also by crosslinking in polymerization via triple bonds. These materials for forming an organic film have excellent heat resistance, but such properties as planarizing property and adhesiveness to a substrate are insufficient and need to be improved.

CITATION LIST

Patent Literature

Patent Document 1: JP 2005-128509 A
Patent Document 2: JP 2006-293298 A
Patent Document 3: JP 2006-285095 A
Patent Document 4: JP 2010-122656 A
Patent Document 5: JP H11-512430 A
Patent Document 6: JP 2005-41938 A
Patent Document 7: JP 2009-206447 A
Patent Document 8: JP 2010-181605 A
Patent Document 9: JP 2012-215842 A
Patent Document 10: WO 2014-208324 A
Patent Document 11: JP 2016-44272 A
Patent Document 12: JP 2016-60886 A
Patent Document 13: JP 2017-14193 A
Patent Document 14: JP 2017-119671 A
Patent Document 15: JP 2018-92170 A

SUMMARY OF INVENTION

Technical Problem

The present invention has been made in view of the above circumstances. An object of the present invention is to provide: a compound which is cured under film formation conditions of air and also inert gas, and which is capable of forming an organic film having not only excellent heat resistance and properties of filling and planarizing a pattern formed on a substrate, but also favorable film formability and adhesiveness to a substrate; and a material for forming an organic film containing the compound. Furthermore, the present invention also provides a substrate for manufacturing a semiconductor device by using the material, a method for forming an organic film using the material, and a patterning process using the material.

Solution to Problem

To solve the above problems, the present invention provides a material for forming an organic film, comprising:

(A) a compound for forming an organic film shown by the following general formula (1A); and (B) an organic solvent, (1A)

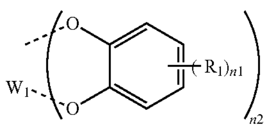

wherein $W_1$ represents a tetravalent or hexavalent organic group, n1 represents an integer of 1 or 2, n2 represents 2 or 3, each $R_1$ independently represents any in the following formula (1B), and a hydrogen atom of a benzene ring in the formula (1A) is optionally substituted with a fluorine atom, (1B)

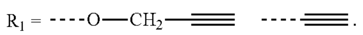

Such a material for forming an organic film is a composition for forming an organic film which is cured under film formation conditions not only in air but also inert gas, and is capable of forming an organic film having high heat resistance, favorable adhesiveness to a substrate, and high filling and planarizing properties.

The component (A) is preferably a compound shown by the following general formula (1C), (1D), or (1E), (1C)

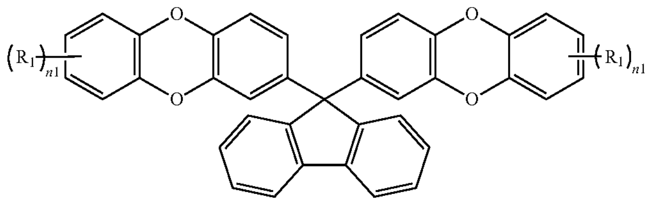

-continued

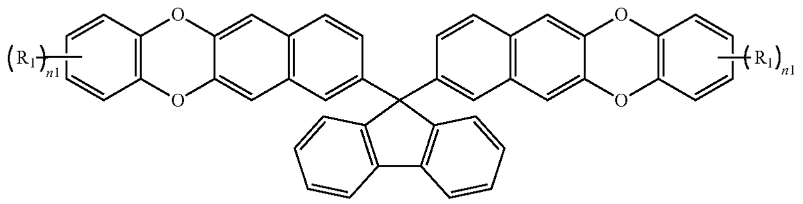

(1D)

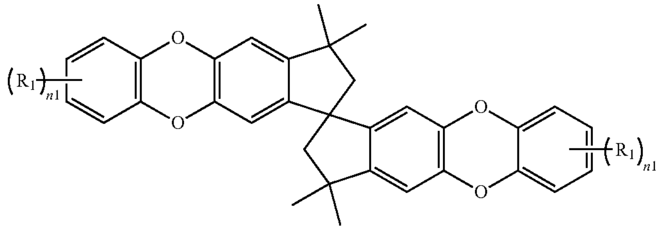

(1E)

wherein n1 and $R_1$ are as defined above.

Introducing a spiro structure or cardo structure into the compound for forming an organic film as described above introduces bendability to the main skeleton, relieves the intermolecular interaction, and inhibits crystallinity. These make it possible to improve solubility in an organic solvent and film formation, and to achieve all of heat resistance and filling/planarizing properties, which are conflicting properties.

Further preferably, the component (A) is a compound shown by the following formula (1F), (1G), or (1H),

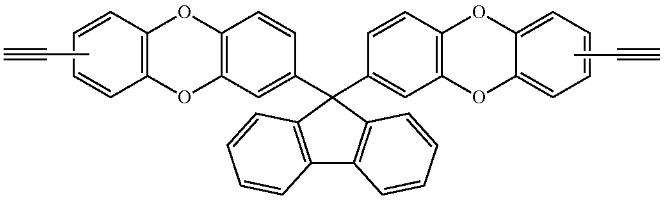

(1F)

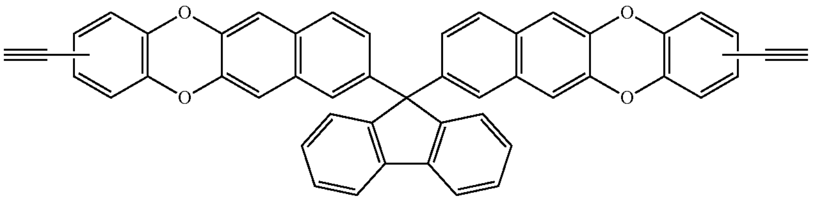

(1G)

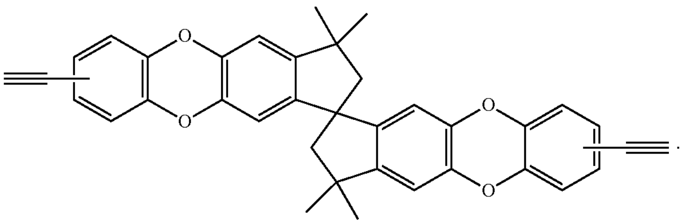

(1H)

The compound for forming an organic film preferably has such a terminal structure as described above in view of heat resistance.

In addition, the component (A) preferably satisfies 1.00≤Mw/Mn≤1.10, where Mw is a weight-average molecular weight and Mn is a number-average molecular weight measured by gel permeation chromatography in terms of polystyrene.

Controlling the Mw/Mn of the compound for forming an organic film within such a range enables formation of an organic film excellent in filling property and planarizing property.

Moreover, the component (B) is preferably a mixture of one or more kinds of organic solvent having a boiling point of lower than 180° C. and one or more kinds of organic solvent having a boiling point of 180° C. or higher.

With such a material for forming an organic film, thermal flowability is imparted to the compound for forming an organic film by the addition of a high-boiling-point solvent. Accordingly, the material for forming an organic film has both higher filling and planarizing properties.

The material for forming an organic film preferably further comprises at least one of (C) an acid generator, (D) a surfactant, (E) a crosslinking agent, and (F) a plasticizer.

The inventive material for forming an organic film may contain one or more of the above components (C) to (F) depending on the purpose.

Further, the present invention provides a substrate for manufacturing a semiconductor device, comprising an organic film on the substrate, the organic film being a cured film of the above-described material for forming an organic film.

The inventive material for forming an organic film has both high filling and planarizing properties, and thereby forms an organic film free from fine pores due to insufficient filling and free from asperity in the organic film surface due to insufficient planarization. The substrate for manufacturing a semiconductor device planarized by the inventive material for forming an organic film has an increased process margin at patterning, making it possible to manufacture semiconductor devices with high yields.

Furthermore, the present invention provides a method for forming an organic film employed in a semiconductor device manufacturing process, the method comprising:

spin-coating a substrate to be processed with the above-described material for forming an organic film; and heating the substrate to be processed coated with the material for forming an organic film under an inert gas atmosphere at a temperature of 50° C. or higher to 600° C. or lower for 10 seconds to 7200 seconds to obtain a cured film.

Additionally, the present invention provides a method for forming an organic film employed in a semiconductor device manufacturing process, the method comprising:

spin-coating a substrate to be processed with the above-described material for forming an organic film;

heating the substrate to be processed coated with the material for forming an organic film in air at a temperature of 50° C. or higher to 300° C. or lower for 5 seconds to 600 seconds to form a coating film; and then performing a heat treatment under an inert gas atmosphere at a temperature of 200° C. or higher to 600° C. or lower for 10 seconds to 7200 seconds to obtain a cured film.

An organic film formed according to any of the inventive methods for forming an organic film and employed in a semiconductor device manufacturing process has high heat resistance, high filling property, and high planarizing property. The use of such an organic film in a semiconductor device manufacturing process allows a favorable semiconductor-device yield.

The inert gas preferably has an oxygen concentration of 1% or less.

Even when heated in such an inert gas atmosphere, the inventive material for forming an organic film is sufficiently cured without generating a sublimation product, and is capable of forming an organic film excellent in adhesiveness to a substrate.

In addition, the substrate to be processed preferably has a structure or a step with a height of 30 nm or more.

The inventive methods for forming an organic film are particularly useful when a flat organic film is formed on such a substrate to be processed.

Moreover, the present invention provides a patterning process comprising:

forming an organic film by using the above-described material for forming an organic film on a substrate to be processed;

forming a silicon-containing resist middle layer film by using a silicon-containing resist middle layer film material on the organic film;

forming a resist upper layer film by using a photoresist composition on the silicon-containing resist middle layer film;

forming a circuit pattern in the resist upper layer film;

transferring the pattern to the silicon-containing resist middle layer film by etching while using the resist upper layer film having the formed pattern as a mask;

transferring the pattern to the organic film by etching while using the silicon-containing resist middle layer film having the transferred pattern as a mask; and further transferring the pattern to the substrate to be processed by etching while using the organic film having the transferred pattern as a mask.

Further, the present invention provides a patterning process comprising:

forming an organic film by using the above-described material for forming an organic film on a substrate to be processed;

forming a silicon-containing resist middle layer film by using a silicon-containing resist middle layer film material on the organic film;

forming an organic antireflective coating on the silicon-containing resist middle layer film;

forming a resist upper layer film by using a photoresist composition on the organic antireflective coating, so that a 4-layered film structure is constructed;

forming a circuit pattern in the resist upper layer film;

transferring the pattern to the organic antireflective coating and the silicon-containing resist middle layer film by etching while using the resist upper layer film having the formed pattern as a mask;

transferring the pattern to the organic film by etching while using the silicon-containing resist middle layer film having the transferred pattern as a mask; and further transferring the pattern to the substrate to be processed by etching while using the organic film having the transferred pattern as a mask.

In addition, the present invention provides a patterning process comprising:

forming an organic film by using the above-described material for forming an organic film on a substrate to be processed;

forming an inorganic hard mask selected from a silicon oxide film, a silicon nitride film, a silicon oxynitride film, a titanium oxide film, and a titanium nitride film on the organic film;

forming a resist upper layer film by using a photoresist composition on the inorganic hard mask;

forming a circuit pattern in the resist upper layer film;

transferring the pattern to the inorganic hard mask by etching while using the resist upper layer film having the formed pattern as a mask;

transferring the pattern to the organic film by etching while using the inorganic hard mask having the transferred pattern as a mask; and further transferring the pattern to the substrate to be processed by etching while using the organic film having the transferred pattern as a mask.

Furthermore, the present invention provides a patterning process comprising:

forming an organic film by using the above-described material for forming an organic film on a substrate to be processed;

forming an inorganic hard mask selected from a silicon oxide film, a silicon nitride film, a silicon oxynitride film, a titanium oxide film, and a titanium nitride film on the organic film;

forming an organic antireflective coating on the inorganic hard mask;

forming a resist upper layer film by using a photoresist composition on the organic antireflective coating, so that a 4-layered film structure is constructed;

forming a circuit pattern in the resist upper layer film;

transferring the pattern to the organic antireflective coating and the inorganic hard mask by etching while using the resist upper layer film having the formed pattern as a mask;

transferring the pattern to the organic film by etching while using the inorganic hard mask having the transferred pattern as a mask; and further transferring the pattern to the substrate to be processed by etching while using the organic film having the transferred pattern as a mask.

The inventive material for forming an organic film can be suitably used for various patterning processes such as a three-layer resist process using a silicon-containing resist middle layer film or an inorganic hard mask, and a four-layer resist process additionally using an organic antireflective coating. In a semiconductor device manufacturing process, a semiconductor device can be manufactured with a high yield by forming a circuit pattern according to the inventive patterning process as described.

In addition, the inorganic hard mask is preferably formed by a CVD method or an ALD method.

In the inventive patterning processes, the inorganic hard mask can be formed by such methods, for example.

Further, the circuit pattern is preferably formed by a lithography using light with a wavelength of 10 nm or more to 300 nm or less, a direct drawing with electron beam, nanoimprinting, or a combination thereof.

In addition, when the circuit pattern is formed, the circuit pattern is preferably developed by alkali development or with an organic solvent.

In the inventive patterning processes, such circuit pattern formation means and development means can be suitably used.

The substrate to be processed is preferably a semiconductor device substrate or the semiconductor device substrate coated with any of a metal film, a metal carbide film, a metal oxide film, a metal nitride film, a metal oxycarbide film, and a metal oxynitride film.

Further, the metal preferably comprises silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

The inventive patterning processes are capable of processing the substrate to be processed as described above to form a pattern.

Moreover, the present invention provides a compound for forming an organic film shown by the following general formula (1A), (1A)

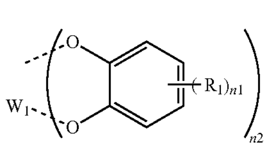

wherein $W_1$ represents a tetravalent or hexavalent organic group, n1 represents an integer of 1 or 2, n2 represents 2 or 3, each $R_1$ independently represents any in the following formula (1B), and a hydrogen atom of a benzene ring in the formula (1A) is optionally substituted with a fluorine atom, (1B)

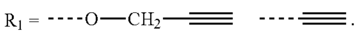

Such a compound cures under film formation conditions not only in air but also inert gas, and is a compound for successfully forming an organic film having high heat resistance and high filling/planarizing properties, as well as excellent adhesiveness to a substrate by the action of dioxin structures, which are oxygen-containing hetero-rings.

Further, the compound for forming an organic film is preferably shown by the following general formula (1C), (1D), or (1E), (1C)

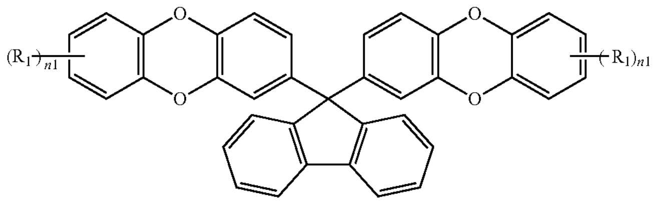

(1D)

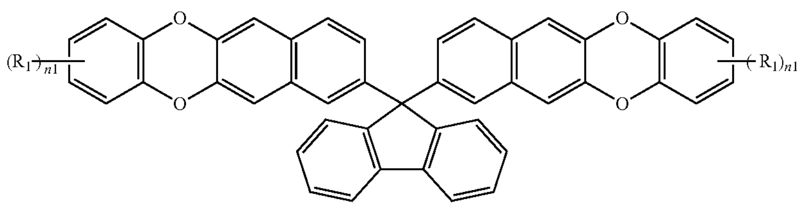

-continued (1E)

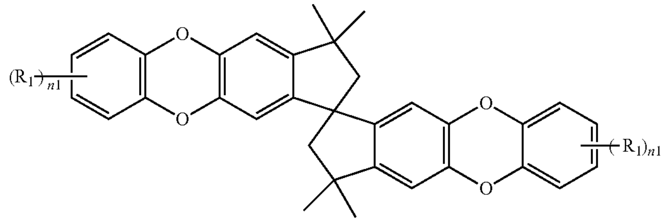

wherein n1 and $R_1$ are as defined above.

Such compounds are capable of imparting excellent solvent solubility by the action of a cardo structure or spiro structure without losing the heat resistance and filling/planarizing properties. Moreover, the compounds for forming an organic film are excellent in film formability regardless of the shape of a substrate to be processed.

In addition, the compound for forming an organic film is preferably shown by the following formula (1F), (1G), or (1H), (1F)

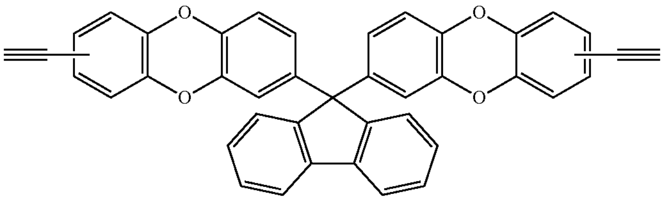

(1G)

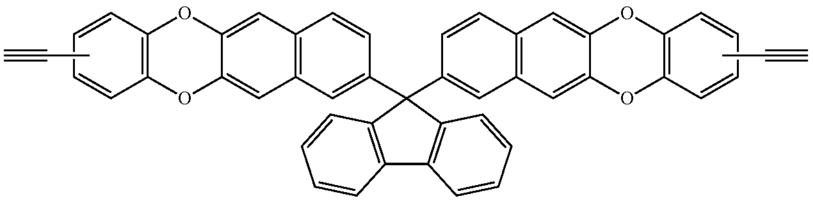

(1H)

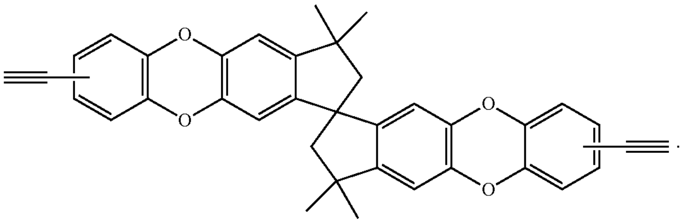

Such compounds are curable under baking conditions in either air or inert gas without generating by-product, and are compounds for forming an organic film that exhibits excellent heat resistance.

Advantageous Effects of Invention

As described above, the inventive compound for forming an organic film is cured without generating a by-product even in film formation in an inert gas for preventing substrate corrosion. The compound is useful for forming an organic film having high filling property, planarizing property, heat resistance, etching resistance, film formability, and adhesiveness. Moreover, an organic film material containing this compound is a material which forms an organic film having excellent filling/planarizing properties and also having various properties such as heat resistance, etching resistance, adhesiveness to a substrate, and film formability. Accordingly, the inventive material for forming an organic film is extremely useful as, for example, an organic film material in multilayer resist methods such as a two-layer resist method, a three-layer resist method using a silicon-containing resist middle layer film, and a four-layer resist method using a silicon-containing resist middle layer film and an organic antireflective coating, or as a planarizing material for manufacturing a semiconductor device. Moreover, an organic film formed from the inventive material for forming an organic film has excellent heat resistance, and therefore, is suitable for patterning since there is no fluctuation in film thickness due to thermal decomposition even when a CVD hard mask is formed on the organic film.

BRIEF DESCRIPTION OF DRAWINGS

FIG. 1 is an explanatory diagram of the planarizing property in the present invention.

FIG. 2 is an explanatory diagram of an example of an inventive patterning process according to a three-layer resist method.

FIG. 3 is an explanatory diagram of a method for evaluating the filling property in Examples.

FIG. 4 is an explanatory diagram of a method for evaluating the planarizing property in Examples.

FIG. 5 is an explanatory diagram of a method for measuring the adhesiveness in Examples.

DESCRIPTION OF EMBODIMENTS

As described above, it has been desired to develop a material for forming an organic film, which generates no by-product under such a film formation condition in an inert gas as to prevent substrate corrosion, for example, even at 300° C. or higher, and which is capable of forming an organic film not only excellent in properties of filling and planarizing a pattern formed on a substrate but also favorable for dry-etching resistance during substrate processing; moreover, the material for forming an organic film causes no fluctuation in film thickness of the organic film due to thermal decomposition even when a CVD hard mask is formed on the organic film. In addition, it has been desired to develop a compound for forming an organic film useful in a patterning process using the material.

Generally, an organic film is formed as follows. A composition is prepared by dissolving a compound for forming an organic film in an organic solvent. Then, a substrate on which a structure, wiring, and so forth of a semiconductor device have been formed is coated with this composition and baked to form an organic film. Immediately after the application of the composition, a coating film is formed along the shape of a step structure on the substrate. Nevertheless, when the coating film is baked, most of the organic solvent is evaporated before curing, so that the organic film is formed from the compound for forming an organic film remaining on the substrate. The present inventors have considered that if the compound for forming an organic film remaining on the substrate has sufficient thermal flowability, the step profile immediately after the application is planarized by thermal flow, and a flat film can be formed.

The present inventors further earnestly studied and consequently found the following. With a compound for forming an organic film shown by the general formula (1A), the action of a substituent shown by $R_1$ provides thermosetting property equivalent to that of a conventional underlayer film material not only in air but also in inert gas. In addition, a partial structure linked with a dioxin ring can provide adhesiveness, thermal flowability, and high filling and planarizing properties. Thus, it is possible to provide a composition for forming an organic film that also has such heat resistance that the composition causes no fluctuation in coating film thickness due to thermal decomposition even when a CVD hard mask is formed. Based on these findings, the present inventors have completed the present invention.

Specifically, the present invention is a material for forming an organic film, comprising:

(A) a compound for forming an organic film shown by the following general formula (1A); and (B) an organic solvent (1A)

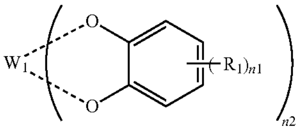

wherein $W_1$ represents a tetravalent or hexavalent organic group, n1 represents an integer of 1 or 2, n2 represents 2 or 3, each $R_1$ independently represents any in the following formula (1B), and a hydrogen atom of a benzene ring in the formula (1A) is optionally substituted with a fluorine atom, (1B)

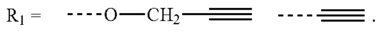

Hereinafter, the present invention will be described in detail. However, the present invention is not limited to the following.

<Compound for Forming Organic Film>

A compound for forming an organic film according to the present invention is a compound shown by the following general formula (1A).

(1A)

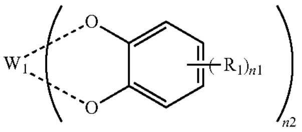

In the formula, $W_1$ represents a tetravalent or hexavalent organic group; n1 represents an integer of 1 or 2; n2 represents an integer of 2 or 3; each $R_1$ independently represents any in the following formula (1B); and a hydrogen atom of a benzene ring may be substituted with a fluorine atom.

(1B)

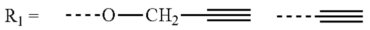

Preferably, $W_1$ in the general formula (1A) has at least one or more aromatic rings, and is bonded to two oxygen atoms as represented by broken lines through substituents on the aromatic ring(s) constituting $W_1$. The bonds between the two oxygen atoms and $W_1$, are preferably such that the oxygen atoms are bonded to positions adjacent to each other on the aromatic ring, thereby forming a 1,4-dioxin ring.

A compound as shown by the general formula (1A) has excellent heat resistance and adhesiveness because of the hetero ring structure thereof. Moreover, it is possible to impart curability in the atmosphere and under an inert gas by the action of a substituent shown by $R_1$. Therefore, an organic film formed using the compound of the present invention makes it possible to prevent defects which would be otherwise generated due to insufficient heat resistance of an organic film, and to prevent film peeling which would otherwise occurs due to insufficient adhesive force, when an inorganic hard mask is formed on the organic film by a CVD method or an ALD method.

Examples of $W_1$ in the general formula (1A) include the following etc. There may be a substituent on the aromatic rings thereof. Examples of the substituent include an alkyl group having 1 to 10 carbon atoms, an alkynyl group and an alkenyl group having 3 to 10 carbon atoms, an aryl group having 6 to 10 carbon atoms, a nitro group, a halogen group, a nitrile group, an alkoxycarbonyl group having 1 to 10 carbon atoms, an alkanoyloxy group having 1 to 10 carbon atoms, etc. In particular, those having a fluorene and spiro ring structure are preferable from the viewpoints of heat resistance and flatness.
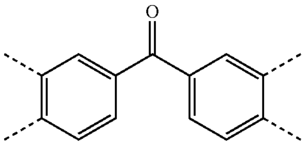
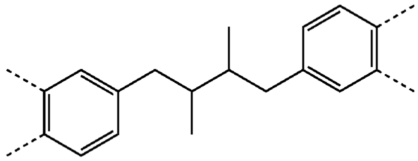
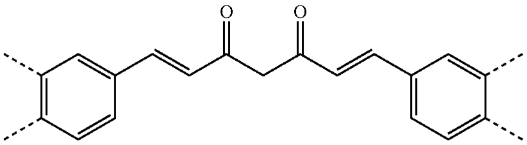
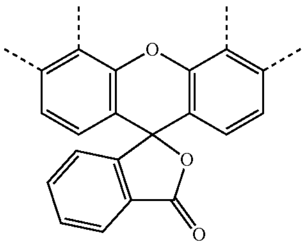
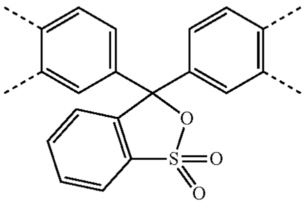
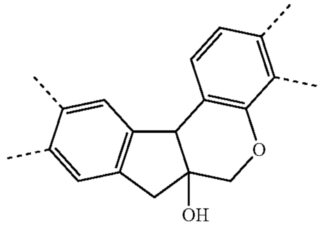
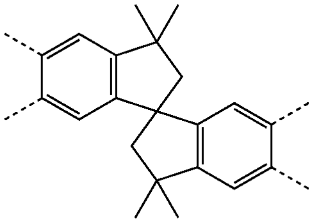
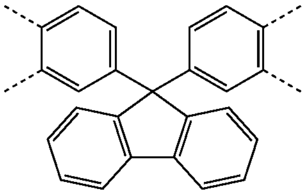
-continued
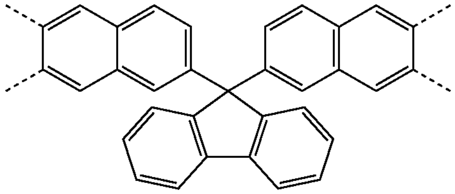
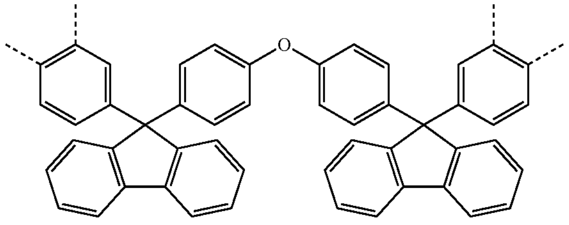
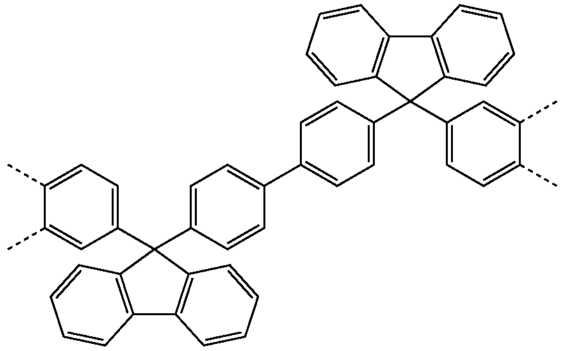
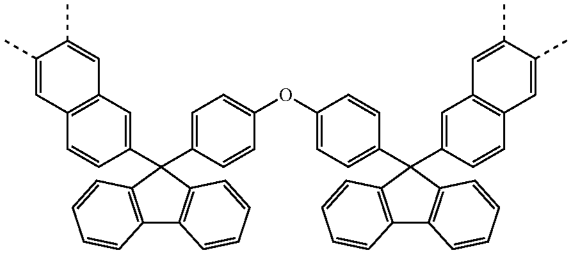
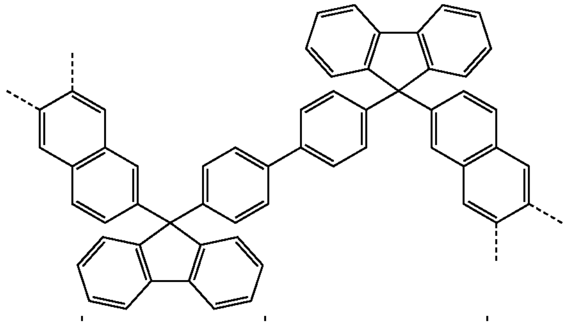
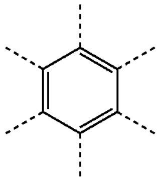
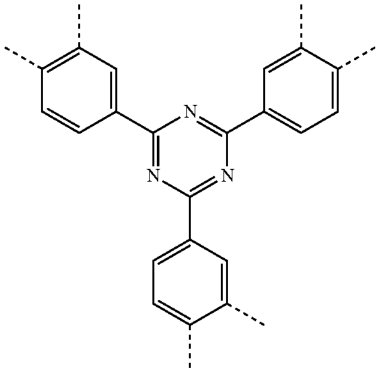

The inventive compound for forming an organic film is preferably a compound having a structure shown by the following general formula (1C), (1D), or (1E).

(1C)

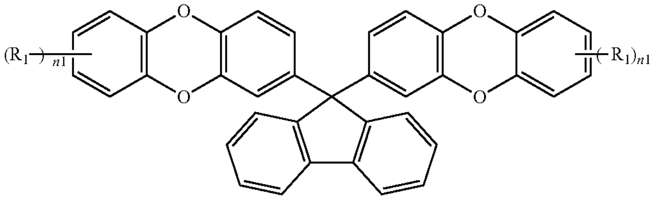

(1D)

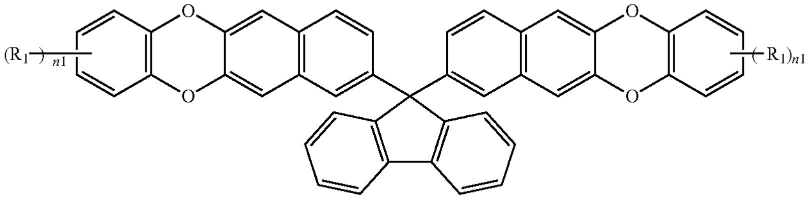

(1E)

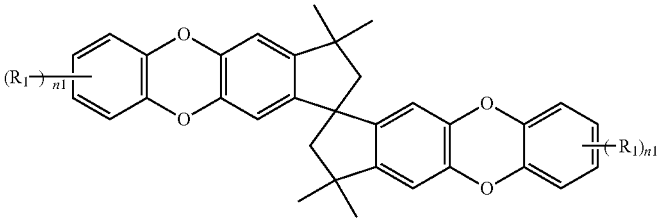

In the formulae, n1 and $R_1$ are as defined above.

The fluorene structure or spiro structure incorporated in the main skeletons shown by the general formulae (1C), (1D), and (1E) makes it possible to impart excellent solubility in an organic solvent, and achieve conflicting properties of heat resistance and filling/planarizing properties.

The inventive compound for forming an organic film is preferably shown by the following formula (1F), (1G), or (1H).

(1F)

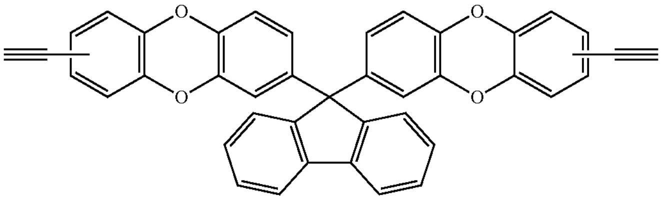

(1G)

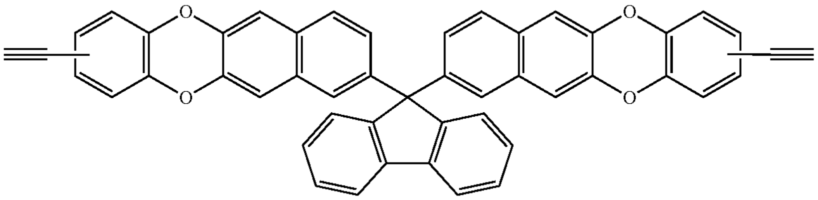

(1H)

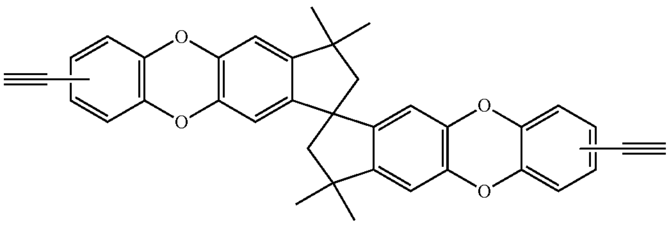

The action of ethynyl groups introduced to terminal structures in the formulae (1F), (1G), and (1H) makes it possible to suppress heat shrinking of a film because by-products are not generated when the organic film is baked and heat-cured.

The inventive compound for forming an organic film preferably satisfies $1.00 \leq Mw/Mn \leq 1.10$ where Mw is a weight-average molecular weight and Mn is a number-average molecular weight in terms of polystyrene measured by gel permeation chromatography.

By controlling the Mw/Mn of the compound for forming an organic film within such a range, an organic film excellent in filling property and planarizing property can be formed.

When the Mw/Mn is within the above range, the thermal flowability of the compound for forming an organic film becomes even more favorable. Therefore, when the compound is blended in a composition, the formed organic film can not only favorably fill a fine structure formed on a substrate but also planarize the entire substrate.

[Method for Manufacturing Compound for Forming Organic Film]

As a method for obtaining the inventive compound for forming an organic film, it is possible to synthesize the compound, for example, by a substitution reaction of a difluorobenzene having the substituent $R_1$ and a tetraol or hexol as shown below with a base catalyst. In this event, each of the tetraol and hexol is preferably a compound having two or three pairs of phenolic hydroxyl groups, the hydroxyl groups constituting one pair being located at positions adjacent to each other on an aromatic ring(s) of the compound as described above. In addition, one kind of the difluorobenzene having the substituent $R_1$ and one kind of the tetraol or hexol may be used in the synthesis, or two or more kinds thereof may be used. These can be appropriately selected and combined according to required properties. $W_1$, $R_1$, n1, and n2 in the following equation are as defined above.

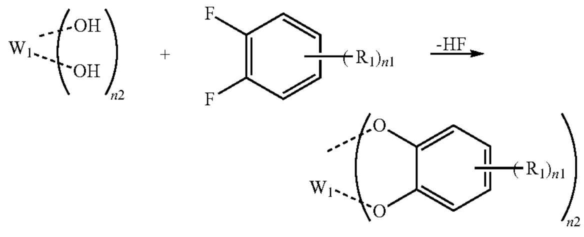

Examples of the base catalyst used in this event include inorganic base compounds, such as sodium hydrogen carbonate, sodium carbonate, potassium carbonate, calcium carbonate, cesium carbonate, sodium hydroxide, potassium hydroxide, sodium hydride, and potassium phosphate; organic amine compounds, such as triethylamine, pyridine, and N-methylmorpholine; etc. One of these or a combination of two or more thereof can be used. The amount of these catalysts used is within a range of preferably 0.1 to 20 moles, more preferably 0.2 to 10 moles, per mol of hydroxyl groups of the raw material tetraol or hexol.

The solvent used in this event is not particularly limited, as long as the solvent is inactive in the reaction. Examples of the solvent include ether-based solvents, such as diethyl ether, tetrahydrofuran, and dioxane; aromatic solvents, such as benzene, toluene, and xylene; acetonitrile, dimethylsulfoxide, N,N-dimethylformamide, N-methylpyrrolidone, water, etc. One of these or a mixture thereof can be used. These solvents can be used within a range of 0 to 2,000 parts by mass relative to 100 parts by mass of the reaction raw materials. The reaction temperature is preferably −50° C. to approximately the boiling point of the solvent, further preferably room temperature to 150° C. The reaction time is appropriately selected from 0.1 to 100 hours.

The reaction method includes: a method in which the difluorobenzene and the tetraol or hexol are charged into a solvent at once; a method in which each or a mixture of the difluorobenzene and the tetraol or hexol is prepared into a form of dispersion or solution and charged dropwise; a method in which one of the difluorobenzene and the tetraol or hexol is dispersed or dissolved in a solvent, and then the other dispersed or dissolved in a solvent is charged dropwise therein; and the like. Furthermore, when multiple kinds of the difluorobenzene and the tetraol or hexol are charged, they can be mixed for reaction beforehand, or they can be made to react individually in succession. Examples of the method with a base catalyst include: a method in which the base catalyst is charged at once with the difluorobenzene or the tetraol or hexol; a method in which the base catalyst prepared in a form of dispersion or solution beforehand is then added dropwise; and the like.

The obtained reaction solution may be diluted with an organic solvent, then subjected to liquid-liquid separation and washing to remove unreacted raw materials, the catalyst, and so on present in the system, and thus collected.

The organic solvent used in the liquid-liquid separation and washing is not particularly limited, as long as the organic solvent is capable of dissolving the compounds and is separated into two layers when mixed with water. The organic solvent includes hydrocarbons, such as hexane, heptane, benzene, toluene, and xylene; esters, such as ethyl acetate, n-butyl acetate, and propylene glycol methyl ether acetate; ketones, such as methyl ethyl ketone, methyl amyl ketone, cyclohexanone, and methyl isobutyl ketone; ethers, such as diethyl ether, diisopropyl ether, methyl-tert-butyl ether, and ethylcyclopentylmethyl ether; chlorinated solvents, such as methylene chloride, chloroform, dichloroethane, and trichloroethylene; mixtures thereof; etc. As washing water used in this event, generally, what is called deionized water or ultrapure water may be used. The washing may be performed one or more times, preferably approximately one to five times because washing ten times or more does not always produce the full washing effects thereof.

In the liquid-liquid separation and washing, the washing may be performed with a basic aqueous solution to remove the unreacted raw materials or acidic components in the system. The base specifically includes hydroxides of alkaline metals, carbonates of alkaline metals, hydroxides of alkali earth metals, carbonates of alkali earth metals, ammonia, organic ammonium, etc.

Further, in the liquid-liquid separation and washing, the washing may be performed with an acidic aqueous solution to remove the unreacted raw materials, metal impurities, or basic components in the system. The acid specifically includes inorganic acids, such as hydrochloric acid, hydrobromic acid, sulfuric acid, nitric acid, phosphoric acid, and heteropoly acid; organic acids, such as oxalic acid, fumaric acid, maleic acid, trifluoroacetic acid, methanesulfonic acid, benzenesulfonic acid, p-toluenesulfonic acid, and trifluoromethanesulfonic acid; etc.

The liquid-liquid separation and washing may be performed with any one of the basic aqueous solution and the acidic aqueous solution, or can be performed with a combination of the two. The liquid-liquid separation and washing is preferably performed with the basic aqueous solution and the acidic aqueous solution in this order from the viewpoint of removing the metal impurities.

After the liquid-liquid separation and washing with the basic aqueous solution and the acidic aqueous solution, washing with neutral water may be successively performed. As the neutral water, deionized water, ultrapure water, or the like as mentioned above may be used. The washing may be performed one or more times, but if the washing is not performed sufficiently, the basic components and acidic components cannot be removed in some cases. The washing is preferably performed approximately one to five times because washing ten times or more does not always produce the full washing effects thereof.

Further, the reaction product after the liquid-liquid separation can also be collected as a powder by concentrating and drying the solvent or crystallizing the reaction product under reduced pressure or normal pressure. Alternatively, the reaction product can also be retained in the state of solution with an appropriate concentration to improve the workability in preparing the material for forming an organic film. The concentration in this event is preferably 0.1 to 50 mass %, more preferably 0.5 to 30 mass %. With such a concentration, the viscosity is hardly increased, making it possible to prevent deterioration of the workability; in addition, since the amount of the solvent is not excessive, it is economical.

The solvent in this event is not particularly limited, as long as the solvent is capable of dissolving the compound. Specific examples of the solvent include ketones, such as cyclohexanone and methyl-2-amyl ketone; alcohols, such as 3-methoxybutanol, 3-methyl-3-methoxybutanol, 1-methoxy-2-propanol, and 1-ethoxy-2-propanol; ethers, such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. One of these or a mixture of two or more thereof can be used.

In the above reaction, the difluorobenzene and the tetraol or hexol can be combined according to a performance requirement. Specifically, it is possible to introduce, for example, a substituent that contributes to solvent solubility, adhesiveness, curability, filling/planarizing properties, etching resistance, and film formability according to a desired performance requirement. An organic film material using these compounds can achieve all of higher filling and planarizing properties as well as higher heat resistance.

As described above, the inventive compound for forming an organic film enables a composition for forming an organic film to have heat resistance to 400° C. or higher and high filling and planarizing properties.

Note that, in the present invention, the term planarizing property refers to a performance of planarizing the surface of a substrate. For example, as shown in FIG. 1, the composition containing the inventive compound for forming an organic film can reduce a 100-nm step of a substrate 1 to 30 nm or less by coating the substrate 1 with a composition 3' for forming an organic film and heating the resultant to form an organic film 3. Note that the step profile shown in FIG. 1 represents a typical example of the step profile in a substrate for manufacturing a semiconductor device. It is a matter of course that the step profile of a substrate which can be planarized by the composition containing the inventive compound for forming an organic film is not limited thereto.

<Material for Forming Organic Film>

Further, the present invention provides a material for forming an organic film (composition for forming an organic film), containing: (A) the inventive compound for forming an organic film shown by the above-described (1A); and (B) an organic solvent. Note that in the inventive material for forming an organic film, one of the above-described inventive compounds for forming an organic film or a combination of two or more thereof can be used.

The organic solvent that can be used in the inventive material for forming an organic film is not particularly limited as long as the solvent can dissolve the compound and other components contained in the material, such as additives. Specifically, solvents with a boiling point of lower than 180° C. can be used, such as those disclosed in paragraphs [0091] and [0092] of JP 2007-199653 A. Above all, propylene glycol monomethyl ether acetate, propylene glycol monomethyl ether, 2-heptanone, cyclopentanone, cyclohexanone, and a mixture of two or more thereof are preferably used. The organic solvent is blended in an amount of preferably 200 to 10,000 parts, more preferably 300 to 5,000 parts, based on 100 parts of the compound (A).

Such a material for forming an organic film can be applied by spin-coating, and has heat resistance to 400° C. or higher and high filling and planarizing properties because the inventive compound for forming an organic film as described above is incorporated.

Further, the inventive material for forming an organic film may use the organic solvent in which a high-boiling-point solvent having a boiling point of 180° C. or higher is added to the aforementioned solvent having a boiling point of lower than 180° C. (a mixture of a solvent having a boiling point of lower than 180° C. and a solvent having a boiling point of 180° C. or higher). The high-boiling-point organic solvent is not particularly limited to hydrocarbons, alcohols, ketones, esters, ethers, chlorinated solvents, and so forth as long as the high-boiling-point organic solvent is capable of dissolving the compound for forming an organic film. Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl-n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, dibutyl succinate, dihexyl succinate, dimethyl adipate, diethyl adipate, dibutyl adipate, and the like. One of these or a mixture thereof may be used.

The boiling point of the high-boiling-point solvent may be appropriately selected according to the temperature at which the material for forming an organic film is heated. The boiling point of the high-boiling-point solvent to be added is preferably 180° C. to 300° C., more preferably 200° C. to 300° C. Such a boiling point prevents the evaporation rate at baking (heating) from becoming excessive, which would otherwise occur if the boiling point is too low. Thus, sufficient thermal flowability can be achieved. Meanwhile, with such a boiling point, the boiling point is not too high, so that the high-boiling-point solvent evaporates after baking and does not remain in the film; thus, the boiling point in these ranges does not adversely affect the film physical properties, such as etching resistance.

When the high-boiling-point solvent is used, the formulation amount of the high-boiling-point solvent is preferably 1 to 30 parts by mass based on 100 parts by mass of the solvent having a boiling point of lower than 180° C. The formulation amount in this range prevents a failure in providing sufficient thermal flowability during baking, which would otherwise occur if the formulation amount is too small. In addition, deterioration of the film physical properties such as etching resistance is prevented, which would otherwise occur if the formulation amount is so large that the solvent remains in the film.

With such a material for forming an organic film, the above-described compound for forming an organic film is provided with thermal flowability by adding the high-boiling-point solvent, so that the material for forming an organic film also has high filling and planarizing properties.

In the inventive material for forming an organic film, (C) an acid generator can be added so as to further promote the curing reaction. The acid generator includes a material that generates an acid by thermal decomposition, and a material that generates an acid by light irradiation. Any acid generator can be added. Specifically, materials disclosed in paragraphs [0061] to [0085] of JP 2007-199653 A can be added, but the present invention is not limited thereto.

One of the acid generators or a combination of two or more thereof can be used. When an acid generator is added, the added amount is preferably 0.05 to 50 parts, more preferably 0.1 to 10 parts, based on 100 parts of the above-described compound.

To the inventive material for forming an organic film, (D) a surfactant can be added so as to enhance the coating property in spin-coating. As the surfactant, for example, those disclosed in [0142] to [0147] of JP 2009-269953 A can be used. When a surfactant is added, the added amount is preferably 0.01 to 10 parts, more preferably 0.05 to 5 parts, based on 100 parts of the above-described compound.

Moreover, to the inventive material for forming an organic film, (E) a crosslinking agent can also be added so as to increase the curability and to further suppress intermixing with an upper layer film. The crosslinking agent is not particularly limited, and known various types of crosslinking agents can be widely used. Examples thereof include melamine-based crosslinking agents, glycoluril-based crosslinking agents, benzoguanamine-based crosslinking agents, urea-based crosslinking agents, β-hydroxyalkylamide-based crosslinking agents, isocyanurate-based crosslinking agents, aziridine-based crosslinking agents, oxazoline-based crosslinking agents, and epoxy-based crosslinking agents.

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the β-hydroxyalkylamide-based crosslinking agents includes N,N,N',N'-tetra(2-hydroxyethyl) adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]. Specific examples of the oxazoline-based crosslinking agents include 2,2'-isopropylidene bis(4-benzyl-2-oxazoline), 2,2'-isopropylidene bis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether. When a crosslinking agent is added, the added amount is preferably 1 to 100 parts, more preferably 5 to 50 parts, based on 100 parts of the above-described compound.

Further, to the inventive material for forming an organic film, (F) a plasticizer can be added so as to further enhance the planarizing and filling properties. The plasticizer is not particularly limited, and known various types of plasticizers can be widely used. Examples thereof include low-molecular-weight compounds, such as phthalic acid esters, adipic acid esters, phosphoric acid esters, trimellitic acid esters, and citric acid esters; and polymers, such as polyethers, polyesters, and polyacetal-based polymers disclosed in JP 2013-253227 A. When a plasticizer is added, the added amount is preferably 1 to 100 parts, more preferably 5 to 30 parts based on 100 parts of the above-described compound.

Furthermore, like the plasticizer, as an additive for providing the inventive material for forming an organic film with filling and planarizing properties, it is preferable to use, for example, liquid additives having polyethylene glycol or polypropylene glycol structures, or thermo-decomposable polymers having a weight loss ratio between 30° C. and 250° C. of 40 mass % or more and a weight average molecular weight of 300 to 200,000. The thermo-decomposable polymers preferably contain a repeating unit having an acetal structure shown by the following general formula (DP1) or (DP1a). When these liquid additives are added, the added amount is preferably 1 to 100 parts, more preferably 5 to 50 parts, based on 100 parts of the above-described compound.

(DP1)

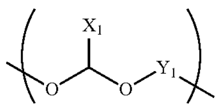

In the formula, $X_1$ represents a hydrogen atom or a saturated or unsaturated monovalent organic group having 1 to 30 carbon atoms which may be substituted. $Y_1$ represents a saturated or unsaturated divalent organic group having 2 to 30 carbon atoms.

(DP1a)

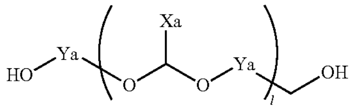

In the formula, $X_a$ represents an alkyl group having 1 to 4 carbon atoms. $Y_a$ represents a saturated or unsaturated divalent hydrocarbon group having 4 to 10 carbon atoms which may have an ether bond. “1” represents an average repeating unit number of 3 to 500.

As described above, the inventive material for forming an organic film has all of heat resistance to 400° C. or higher and high filling and planarizing properties. Thus, the inventive material for forming an organic film is extremely useful as a material for forming an organic film in multilayer resist methods, such as a two-layer resist method, a three-layer resist method using a silicon-containing resist middle layer film or inorganic hard mask, and a four-layer resist method using a silicon-containing resist middle layer film or inorganic hard mask and an organic antireflective coating. Moreover, the inventive material for forming an organic film generates no by-product even during film formation in an inert gas, and has excellent filling and planarizing properties. Accordingly, the inventive material for forming an organic film can also be suitably used as a planarizing material in a semiconductor device manufacturing process, besides the multilayer resist methods.

<Substrate for Manufacturing Semiconductor Device>

Additionally, the present invention provides a substrate for manufacturing a semiconductor device, including an organic film formed on the substrate, the organic film being formed by curing the above-described material for forming an organic film.

An organic film formed with the inventive material for forming an organic film has both high filling and planarizing properties, and is therefore an organic film free from fine pores due to insufficient filling and free from asperity in the organic film surface due to insufficient planarizing. Thus, a semiconductor device substrate planarized with such an organic film has an increased process margin at patterning, making it possible to manufacture semiconductor devices with high yields.

<Method for Forming Organic Film>

The present invention provides a method for forming an organic film employed in a semiconductor device manufacturing process, the method including:

spin-coating a substrate to be processed with the above-described material for forming an organic film;

heating the substrate to be processed coated with the material for forming an organic film under an inert gas atmosphere at a temperature of 50° C. or higher to 600° C. or lower for 10 seconds to 7200 seconds to obtain a cured film (one-stage baking).

Moreover, the present invention provides a method for forming an organic film capable of planarizing the surface of a stepped substrate used in a semiconductor device manufacturing process, the method including:

spin-coating a substrate to be processed with the above-described inventive material for forming an organic film;

heating the substrate to be processed coated with the material for forming an organic film in air at a temperature of 50° C. or higher to 300° C. or lower for 5 to 600 seconds to form a coating film; and then performing a heat treatment under an inert gas atmosphere at a temperature of 200° C. or higher to 600° C. or lower, preferably 250° C. or higher, for 10 to 7200 seconds to obtain a cured film (two-stage baking).

In these methods for forming an organic film, first, a substrate to be processed is spin-coated with the above-described inventive material for forming an organic film. By employing the spin-coating method, favorable filling property can be obtained. After the spin-coating, baking (heating) is performed to promote the planarization attributable to thermal flow and the crosslinking reaction. Note that since this baking allows the solvent in the material for forming an organic film to evaporate, even when a resist upper layer film or a silicon-containing resist middle layer film is formed on the organic film, the mixing thereof can be prevented.

The film formation step by heating to form an organic film (organic underlayer film) can employ one-stage baking, two-stage baking, or multi-stage baking of three or more stages. Nevertheless, one-stage baking or two-stage baking is economically preferable.

The film formation by the one-stage baking is performed under an inert gas atmosphere at a temperature of 50° C. or higher to 600° C. or lower for 10 to 7200 seconds, preferably at a temperature of 150° C. or higher to 500° C. or lower for 10 to 3600 seconds. Heating under such conditions can promote the planarization attributable to thermal flow and the crosslinking reaction.

In a multilayer resist method, a coating-type silicon-containing resist middle layer film or a CVD hard mask is sometimes formed on a film thus obtained. In the case where a coating-type silicon-containing resist middle layer film is employed, the organic film is formed preferably at a temperature higher than a temperature at which the silicon-containing resist middle layer film is formed. Generally, a silicon-containing resist middle layer film is formed at 100° C. or higher to 400° C. or lower, preferably 150° C. or higher to 350° C. or lower. Forming the organic film at a temperature higher than these temperatures makes it possible to prevent a composition for forming the silicon-containing resist middle layer film from dissolving the organic film, and to form an organic film not mixed with the composition. In the case where a CVD hard mask is employed, the organic film is formed preferably at a temperature higher than a temperature at which the CVD hard mask is formed. Examples of the temperature at which the CVD hard mask is formed include temperatures at 150° C. or higher to 500° C. or lower.

On the other hand, in film formation by the two-stage baking, the first baking is performed in air at the treatment temperature of 50° C. or higher to 300° C. or lower, preferably 250° C. or lower, for 5 to 600 seconds, considering the influence of substrate corrosion due to oxygen in air. The second baking is performed in an inert gas, and the baking temperature is higher than the first baking temperature. The second baking is performed at a temperature of 200° C. or higher to 600° C. or lower, preferably 250° C. or higher to 500° C. or lower, for 10 to 7200 seconds.

In a multilayer resist method, a coating-type silicon-containing resist middle layer film or a CVD hard mask is sometimes formed on a film thus obtained. In the case where a coating-type silicon-containing resist middle layer film is employed, the organic film is formed preferably at a temperature higher than a temperature at which the silicon-containing resist middle layer film is formed. Generally, a silicon-containing resist middle layer film is formed at 100° C. or higher to 400° C. or lower, preferably 150° C. or higher to 350° C. or lower. Forming the organic film at a temperature higher than these temperatures makes it possible to prevent a composition for forming the silicon-containing resist middle layer film from dissolving the organic film, and to form an organic film not mixed with the composition. In the case where a CVD hard mask is employed in the two-stage baking, the organic film is formed preferably at a temperature higher than a temperature at which the CVD hard mask is formed. Examples of the temperature at which the CVD hard mask is formed include temperatures at 150° C. or higher to 500° C. or lower.

In addition, the present invention provides a method for forming an organic film that functions as an organic underlayer film used in a semiconductor device manufacturing process, where a cured film is formed by heating a substrate to be processed in an atmosphere with an oxygen concentration of 1% or less to prevent corrosion of the substrate to be processed.

In this method for forming an organic film, first of all, a substrate to be processed is spin-coated with the above-described inventive material for forming an organic film. After the spin-coating, in the two-stage baking, first, the first baking is performed in air at 300° C. or lower. Then, the second baking is performed under an atmosphere with an oxygen concentration of 1% or less. In the one-stage baking, the first baking in air can be skipped. Note that examples of the atmosphere during the baking include such inert gases as nitrogen, argon, and helium. The inventive material for forming an organic film is capable of forming a sufficiently cured organic film without generating a sublimation product, even when the baking is performed under such an inert gas atmosphere.

Moreover, the inventive methods for forming an organic film make it possible to use a substrate to be processed having a structure or a step with a height of 30 nm or more. As described above, since the inventive material for forming an organic film is excellent in filling and planarizing properties, even when the substrate to be processed has a structure or a step (asperity) with a height of 30 nm or more, a flat cured film can be formed. That is, the inventive methods for forming an organic film are particularly useful when a flat organic film is formed on such a substrate to be processed.

Note that the thickness of the organic film to be formed is appropriately selected, but is preferably 30 to 20,000 nm, particularly preferably 50 to 15,000 nm.

Additionally, the above-described methods for forming an organic film by the inventive material for forming an organic film are applicable to both cases where an organic film for an organic underlayer film is formed, and where an organic film for a flat film is formed.

<Patterning Processes>

[3-Layer Resist Method using Silicon-Containing Resist Middle Layer Film]

The present invention provides a patterning process including:

- forming an organic film by using the above-described inventive material for forming an organic film on a substrate to be processed;
- forming a silicon-containing resist middle layer film by using a silicon-containing resist middle layer film material containing silicon atoms on the organic film;
- forming a resist upper layer film by using a photoresist composition as a resist upper layer film material on the silicon-containing resist middle layer film;
- forming a circuit pattern in the resist upper layer film;
- transferring the pattern to the silicon-containing resist middle layer film by etching while using the resist upper layer film having the formed circuit pattern as a mask;
- transferring the pattern to the organic film by etching while using the silicon-containing resist middle layer film having the transferred pattern as a mask; and
- further transferring the pattern to the substrate to be processed by etching while using the organic film having the transferred pattern as a mask.

As the substrate to be processed, it is preferable to use a semiconductor device substrate or the semiconductor device substrate coated with any of a metal film, a metal carbide film, a metal oxide film, a metal nitride film, a metal oxycarbide film, and a metal oxynitride film. More specifically, examples of the substrate which may be used include, but are not particularly limited to: substrates made of Si, α-Si, p-Si, $SiO_2$, SiN, SiON, W, TiN, Al, or the like; and these substrates coated with the above-described metal film or the like as a layer to be processed.

Examples of the layer to be processed which may be used include various Low-k films made of Si, $SiO_2$, SiON, SiN, p-Si, α-Si, W, W—Si, Al, Cu, Al—Si, or the like, and stopper films thereof. The layer can be formed to have a thickness of generally 50 to 10,000 nm, particularly 100 to 5,000 nm. Note that when the layer to be processed is formed, the substrate and the layer to be processed are formed from different materials.

Note that it is preferable to use, as the metal on the substrate to be processed, silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

Further, as the substrate to be processed, a substrate to be processed having a structure or a step with a height of 30 nm or more is preferably used.

When the organic film is formed on the substrate to be processed using the inventive material for forming an organic film, the above-described inventive methods for forming an organic film can be employed.

Next, using a resist middle layer film material containing silicon atoms, a resist middle layer film (silicon-containing resist middle layer film) is formed on the organic film. The silicon-containing resist middle layer film material is preferably a polysiloxane-based middle layer film material. The silicon-containing resist middle layer film having an antireflective effect can suppress the reflection. Particularly, for 193-nm light exposure, a material containing many aromatic groups and having a high etching selectivity relative to the substrate is used as a material for forming an organic film, so that the k-value and thus the substrate reflection are increased. Meanwhile, the reflection can be suppressed by imparting absorption to the silicon-containing resist middle layer film so as to have an appropriate k-value, and the substrate reflection can be reduced to 0.5% or less. As the silicon-containing resist middle layer film having an antireflective effect, a polysiloxane is preferably used which has anthracene for 248-nm and 157-nm light exposure, or a phenyl group or a light-absorbing group having a silicon-silicon bond for 193-nm light exposure in a pendant structure or a polysiloxane structure, and which is crosslinked by an acid or heat.

Next, using a resist upper layer film material composed of a photoresist composition, a resist upper layer film is formed on the silicon-containing resist middle layer film. The resist upper layer film material may be a positive type or a negative type, and any generally-used photoresist composition can be used. After the spin-coating of the resist upper layer film material, pre-baking is preferably performed at 60 to 180° C. for 10 to 300 seconds. Then, light exposure, and furthermore, post-exposure bake (PEB), and development are performed according to conventional methods to obtain a resist upper layer film pattern. Note that the thickness of the resist upper layer film is not particularly limited, but is preferably 30 to 500 nm, particularly preferably 50 to 400 nm.

Next, a circuit pattern (the resist upper layer film pattern) is formed in the resist upper layer film. The circuit pattern is preferably formed by a lithography using light with a wavelength of 10 nm or more to 300 nm or less, a direct drawing with electron beam, nanoimprinting, or a combination thereof.

Note that the exposure light includes high energy beam with a wavelength of 300 nm or less; specifically, deep ultraviolet ray, KrF excimer laser beam (248 nm), ArF excimer laser beam (193 nm), $F_2$ laser beam (157 nm), $Kr_2$ laser beam (146 nm), Are laser beam (126 nm), soft X-ray (EUV) with a wavelength of 3 to 20 nm, electron beam (EB), ion beam, X-ray, etc.

Furthermore, when the circuit pattern is formed, the circuit pattern is preferably developed by alkaline development or with an organic solvent.

Next, the pattern is transferred to the silicon-containing resist middle layer film by etching while using the resist upper layer film having the formed circuit pattern as a mask. The etching of the silicon-containing resist middle layer film while using the resist upper layer film pattern as a mask is preferably performed with a fluorocarbon-based gas. Thereby, a silicon-containing resist middle layer film pattern is formed.

Next, the pattern is transferred to the organic film by etching while using the silicon-containing resist middle layer film having the transferred pattern as a mask. Since the silicon-containing resist middle layer film exhibits higher etching resistance to an oxygen gas or a hydrogen gas than that of an organic material, the etching of the organic film while using the silicon-containing resist middle layer film pattern as a mask is preferably performed with an etching gas mainly containing an oxygen gas or a hydrogen gas. Thereby, an organic film pattern can be formed.

Next, the pattern is transferred to the substrate to be processed by etching while using the organic film having the transferred pattern as a mask. The etching of the substrate to be processed (layer to be processed) can be performed according to a conventional method. For example, the substrate to be processed made of $SiO_2$, SiN, or silica low-dielectric insulating film is etched mainly with a fluorocarbon-based gas. The substrate to be processed made of p-Si, Al, or W is etched mainly with a chlorine- or bromine-based gas. When the substrate is processed by etching with a fluorocarbon-based gas, the silicon-containing resist middle layer film pattern is removed together with the substrate processing. Meanwhile, when the substrate is processed by etching with a chlorine- or bromine-based gas, the silicon-containing resist middle layer film pattern needs to be removed by additional dry-etching with a fluorocarbon-based gas after the substrate processing.

The organic film obtained using the inventive material for forming an organic film can exhibit excellent etching resistance when the substrate to be processed is etched as described above.

[4-Layer Resist Method using Silicon-Containing Resist Middle Layer Film and Organic Antireflective Coating]

Moreover, the present invention provides a patterning process including:

- forming an organic film by using the above-described inventive material for forming an organic film on a substrate to be processed;
- forming a silicon-containing resist middle layer film by using a resist middle layer film material containing silicon atoms on the organic film;
- forming an organic antireflective coating on the silicon-containing resist middle layer film;
- forming a resist upper layer film by using a photoresist composition as a resist upper layer film material on the organic antireflective coating;
- forming a circuit pattern in the resist upper layer film;
- transferring the pattern to the organic antireflective coating and the silicon-containing resist middle layer film by dry-etching while using the resist upper layer film having the formed circuit pattern as a mask;
- transferring the pattern to the organic film by etching while using the silicon-containing resist middle layer film having the transferred pattern as a mask; and
- further transferring the pattern to the substrate to be processed by etching while using the organic film having the transferred pattern as a mask.

Note that this method can be performed in the same manner as the above-described three-layer resist method using the silicon-containing resist middle layer film, except that the organic antireflective coating (BARC) is formed between the silicon-containing resist middle layer film and the resist upper layer film.

The organic antireflective coating can be formed by spin-coating using a known organic antireflective coating material.

[3-Layer Resist Method Using Inorganic Hard Mask]

Further, as a patterning process by a three-layer resist method using the above-described inventive material for forming an organic film, the present invention provides a patterning process including:

- forming an organic film by using the above-described inventive material for forming an organic film on a substrate to be processed;
- forming an inorganic hard mask selected from a silicon oxide film, a silicon nitride film, a silicon oxynitride film, a titanium oxide film, and a titanium nitride film on the organic film;
- forming a resist upper layer film by using a photoresist composition as a resist upper layer film material on the inorganic hard mask;
- forming a circuit pattern in the resist upper layer film;
- transferring the pattern to the inorganic hard mask by etching while using the resist upper layer film having the formed circuit pattern as a mask;
- transferring the pattern to the organic film by etching while using the inorganic hard mask having the transferred pattern as a mask; and
- further transferring the pattern to the substrate to be processed by etching while using the organic film having the transferred pattern as a mask.

Note that this method can be performed in the same manner as the above-described three-layer resist method using the silicon-containing resist middle layer film, except that the inorganic hard mask is formed in place of the silicon-containing resist middle layer film on the organic film.

The inorganic hard mask selected from a silicon oxide film, a silicon nitride film, a silicon oxynitride film (SiON film), a titanium oxide film, and a titanium nitride film can be formed by a CVD method, an ALD method, etc. The method for forming the silicon nitride film is disclosed in, for example, JP 2002-334869 A, WO 2004/066377 A1, etc. The film thickness of the inorganic hard mask is preferably 5 to 200 nm, more preferably 10 to 100 nm. As the inorganic hard mask, a SiON film is most preferably used which is effective as an antireflective coating. When the SiON film is formed, the substrate temperature reaches 300 to 500° C. Hence, the organic film needs to withstand the temperature of 300 to 500° C. Since the organic film formed using the composition for forming an organic film of the present invention has high heat-resistance and can withstand high temperatures of 300° C. to 500° C., this enables the combination of the inorganic hard mask formed by a CVD method or an ALD method with the organic film formed by a spin-coating method.

[4-Layer Resist Method using Inorganic Hard Mask and Organic Antireflective Coating]

Furthermore, as a patterning process by a four-layer resist method using the above-described inventive material for forming an organic film, the present invention provides a patterning process including:

- forming an organic film by using the above-described inventive material for forming an organic film on a substrate to be processed;
- forming an inorganic hard mask selected from a silicon oxide film, a silicon nitride film, a silicon oxynitride film, a titanium oxide film, and a titanium nitride film on the organic film;
- forming an organic antireflective coating on the inorganic hard mask;
- forming a resist upper layer film by using a photoresist composition as a resist upper layer film material on the organic antireflective coating;
- forming a circuit pattern in the resist upper layer film;
- transferring the pattern to the organic antireflective coating and the inorganic hard mask by etching while using the resist upper layer film having the formed circuit pattern as a mask;
- transferring the pattern to the organic film by etching while using the inorganic hard mask having the transferred pattern as a mask; and
- further transferring the pattern to the substrate to be processed by etching while using the organic film having the transferred pattern as a mask.

Note that this method can be performed in the same manner as the above-described three-layer resist method using the inorganic hard mask, except that the organic antireflective coating (BARC) is formed between the inorganic hard mask and the resist upper layer film.

Particularly, when the SiON film is used as the inorganic hard mask, two antireflective coatings including the SiON film and the BARC make it possible to suppress the reflection even in liquid immersion exposure at a high NA exceeding 1.0. Another merit of the BARC formation is having an effect of reducing footing of the resist upper layer film pattern immediately above the SiON film.

Herein, FIG. 2 (A) to (F) show an example of the inventive patterning process according to the three-layer resist method. In the three-layer resist method, as shown in FIG. 2 (A), using the inventive material for forming an organic film, an organic film 3 is formed on a layer 2 to be processed formed on a substrate 1. Then, a silicon-containing resist middle layer film 4 is formed, and a resist upper layer film 5 is formed thereon. Subsequently, as shown in FIG. 2 (B), a portion 6 to be exposed of the resist upper layer film 5 is exposed to light, followed by PEB (post-exposure bake). Thereafter, as shown in FIG. 2 (C), a resist upper layer film pattern 5*a* is formed by development. After that, as shown in FIG. 2 (D), using the resist upper layer film pattern 5*a* as a mask, the silicon-containing resist middle layer film 4 is processed by dry-etching with a fluorocarbon-based gas. Thereby, a silicon-containing resist middle layer film pattern 4*a* is formed. Then, as shown in FIG. 2 (E), after the resist upper layer film pattern 5*a* is removed, the organic film 3 is etched with oxygen plasma while using the silicon-containing resist middle layer film pattern 4*a* as a mask. Thereby, an organic film pattern 3*a* is formed. Further, as shown in FIG. 2 (F), after the silicon-containing resist middle layer film pattern 4*a* is removed, the layer 2 to be processed is processed by etching while using the organic film pattern 3*a* as a mask. Thus, a pattern 2*a* is formed.

In the case where an inorganic hard mask is formed, the silicon-containing resist middle layer film 4 may be replaced with the inorganic hard mask. In the case where a BARC is formed, the BARC may be formed between the silicon-containing resist middle layer film 4 and the resist upper layer film 5. The etching of the BARC starts before the etching of the silicon-containing resist middle layer film 4, but these etchings may be performed continuously. Alternatively, after the BARC is etched alone, the etching apparatus is changed, for example, and then the silicon-containing resist middle layer film 4 may be etched.

As described above, the inventive patterning processes make it possible to precisely form a fine pattern in a substrate to be processed by the multilayer resist methods.

EXAMPLE

Hereinafter, the present invention will be more specifically described with reference to Synthesis Examples, Examples, and Comparative Examples. However, the present invention is not limited thereto. Note that, with respect to molecular weight and dispersity, weight-average molecular weight (Mw) and number-average molecular weight (Mn) were measured by gel permeation chromatography (GPC) using tetrahydrofuran as an eluent in terms of polystyrene, and dispersity (Mw/Mn) was calculated therefrom.

SYNTHESIS EXAMPLES: SYNTHESIS OF COMPOUNDS FOR MATERIAL FOR FORMING ORGANIC FILM

Compounds (A1) to (A7) for organic film materials were synthesized using tetraol or hexol: (B1) to (B4) and fluorobenzene: (C1) to (C3) shown below. Moreover, comparative raw materials (D1) to (D7) were used in synthesis of Compounds (R1) to (R5) for Comparative Examples.

Tetraol or Hexol:
(B1)
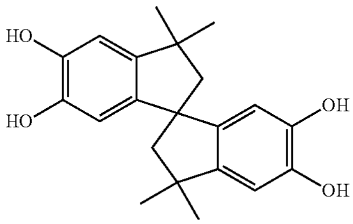
(B2)
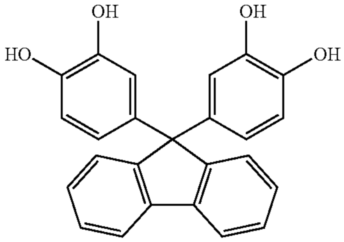
(B3)
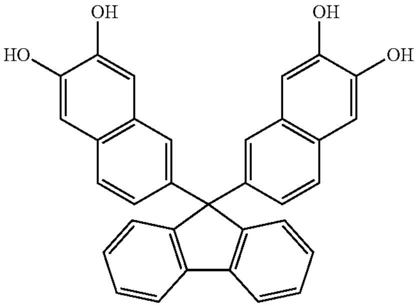
(B4)
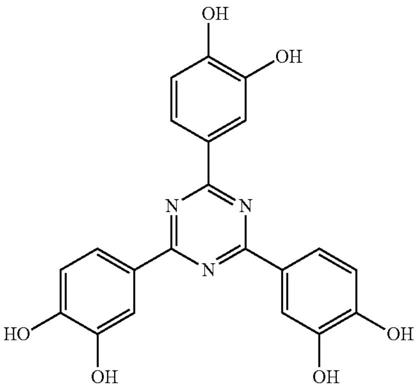
Fluorobenzene:
(C1)
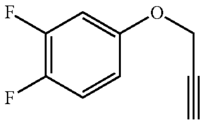
(C2)
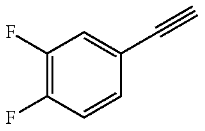
-continued
(C3)
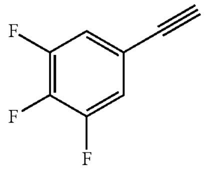
Raw materials for Synthesis in Comparative Examples:
(D1)
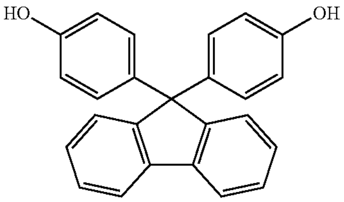
(D2)
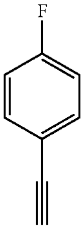
(D3)
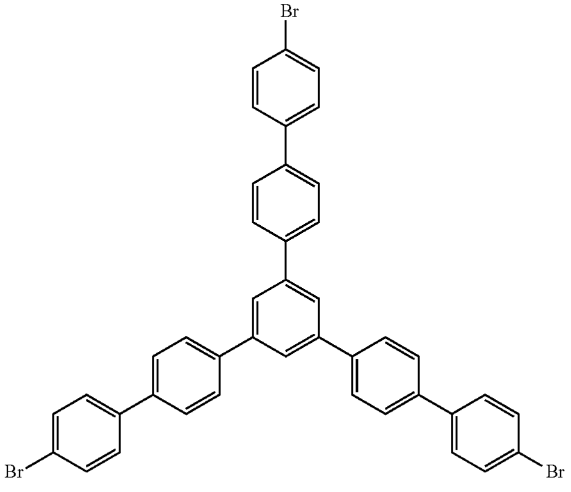
(D4)
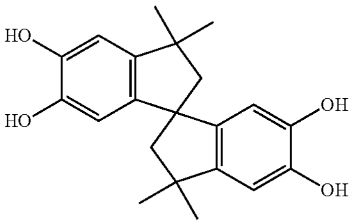

-continued (D5)

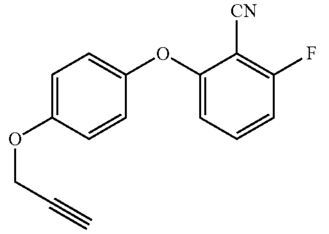

(D6)

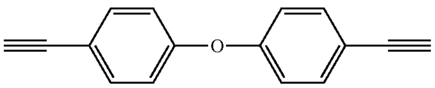

(D7)

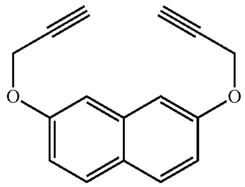

[Synthesis Example 1] Synthesis of Compound (A1)

To 20.0 g of tetraol (B1), 24.7 g of fluorobenzene (C1), and 36.0 g of potassium carbonate, 200 g of N-methylpyrrolidone was added for reaction with an inner temperature of 160° C. for 24 hours under nitrogen atmosphere. After cooling at room temperature, 300 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 300 g of hexane. The precipitated crystal was separated by filtration, washed twice with 200 g of hexane, and collected. The collected crystal was vacuum dried at 70° C. Thus, (A1) was obtained as a mixture shown below. The isomer ratio determined by LC is also shown. Additionally, when the weight-average molecular weight (Mw) and dispersity (Mw/Mn) were measured by GPC, the following results were obtained.

(A1): Mw=640, Mw/Mn=1.03

(A1)

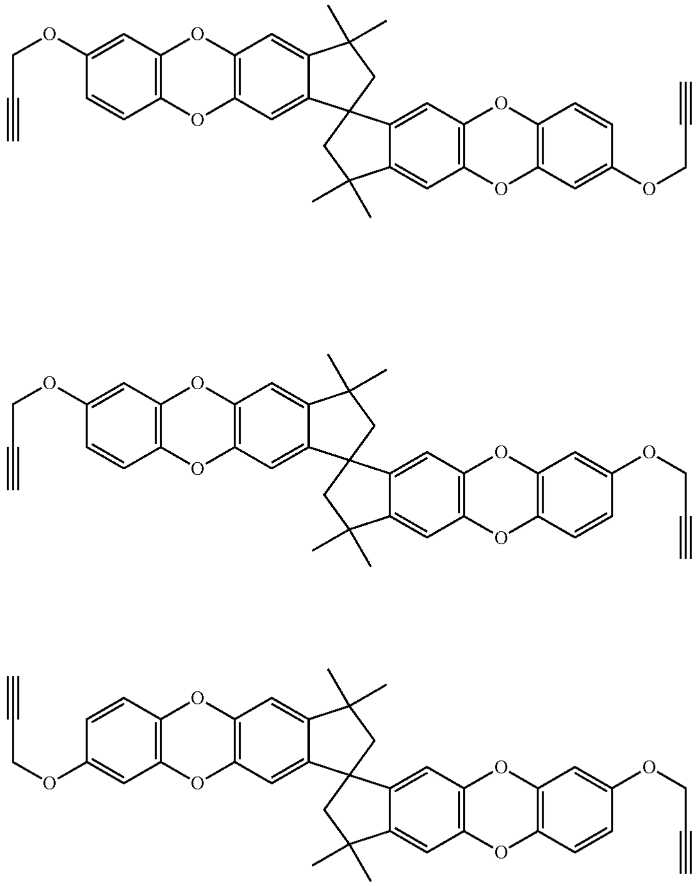

[Synthesis Example 2] Synthesis of Compound (A2)

To 20.0 g of tetraol (B1), 20.3 g of fluorobenzene (C2), and 36.0 g of potassium carbonate, 200 g of N-methylpyrrolidone was added for reaction with an inner temperature of 140° C. for 24 hours under nitrogen atmosphere. After cooling at room temperature, 300 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 300 g of hexane. The precipitated crystal was separated by filtration, washed twice with 200 g of hexane, and collected. The collected crystal was vacuum dried at 70° C. Thus, (A2) was obtained as a mixture shown below. The isomer ratio determined by LC is also shown. Additionally, when the weight-average molecular weight (Mw) and dispersity (Mw/Mn) were measured by GPC, the following results were obtained.

(A2): Mw=570, Mw/Mn=1.05

[Synthesis Example 3] Synthesis of Compound (A3)

To 20.0 g of tetraol (B2), 22.3 g of fluorobenzene (C1), and 32.1 g of potassium carbonate, 200 g of N-methylpyrrolidone was added for reaction with an inner temperature of 160° C. for 24 hours under nitrogen atmosphere. After cooling at room temperature, 300 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 300 g of hexane. The precipitated crystal was separated by filtration, washed twice with 200 g of hexane, and collected. The collected crystal was vacuum dried at 70° C. Thus, (A3) was obtained as a mixture shown below. The isomer ratio determined by LC is also shown. Additionally, when the weight-average molecular weight (Mw) and dispersity (Mw/Mn) were measured by GPC, the following results were obtained.

(A3): Mw=670, Mw/Mn=1.02

(A2)

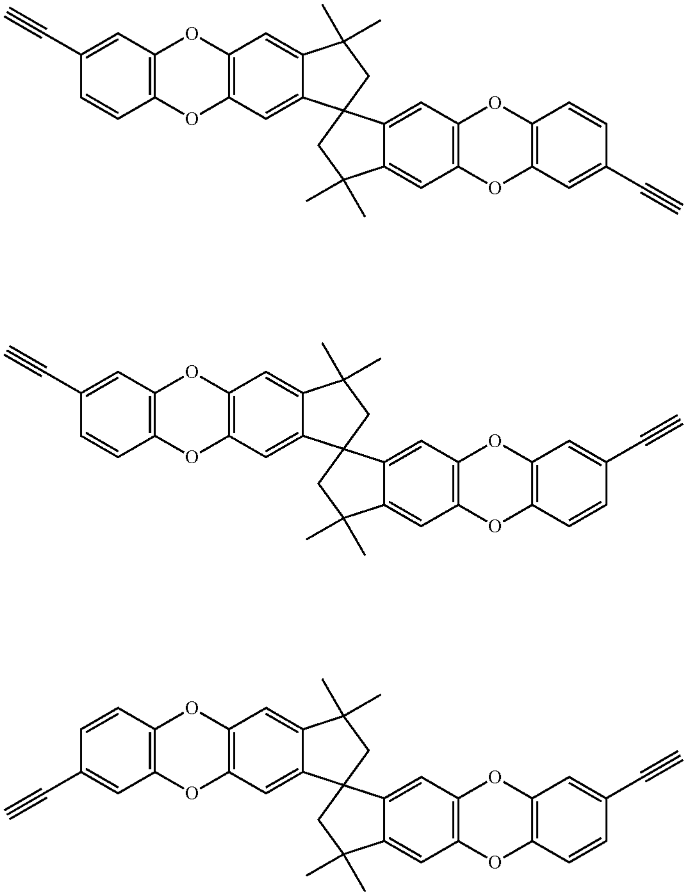

27:46:27

(A3)

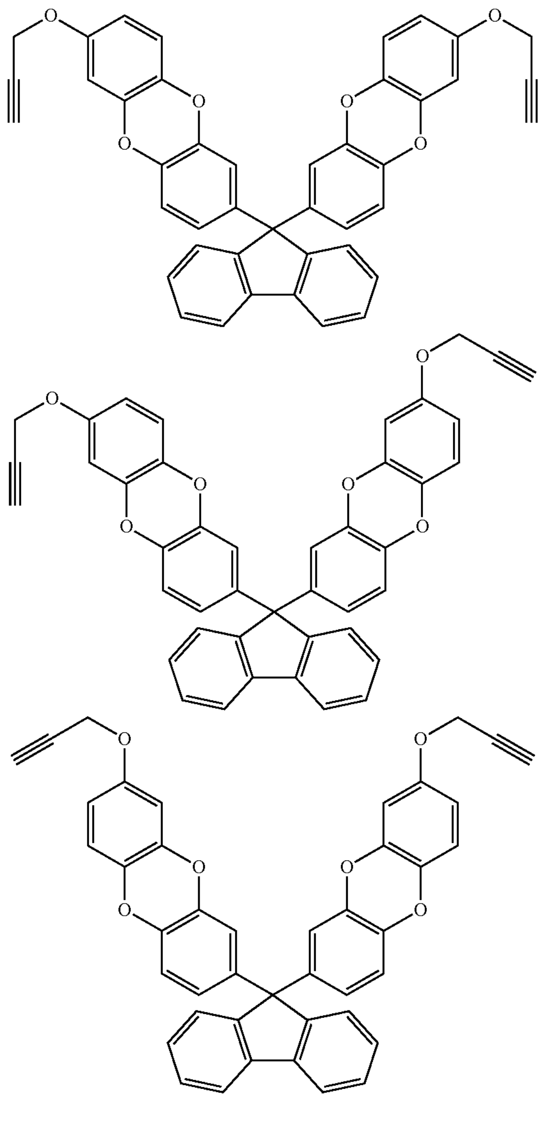

26:48:26

[Synthesis Example 4] Synthesis of Compound (A4)

To 20.0 g of tetraol (B2), 18.1 g of fluorobenzene (C2), and 32.1 g of potassium carbonate, 200 g of N-methylpyrrolidone was added for reaction with an inner temperature of 140° C. for 24 hours under nitrogen atmosphere. After cooling at room temperature, 300 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 300 g of hexane. The precipitated crystal was separated by filtration, washed twice with 200 g of hexane, and collected. The collected crystal was vacuum dried at 70° C. Thus, (A4) was obtained as a mixture shown below. The isomer ratio determined by LC is also shown. Additionally, when the weight-average molecular weight (Mw) and dispersity (Mw/Mn) were measured by GPC, the following results were obtained.

(A4): Mw=610, Mw/Mn=1.04

(A4)

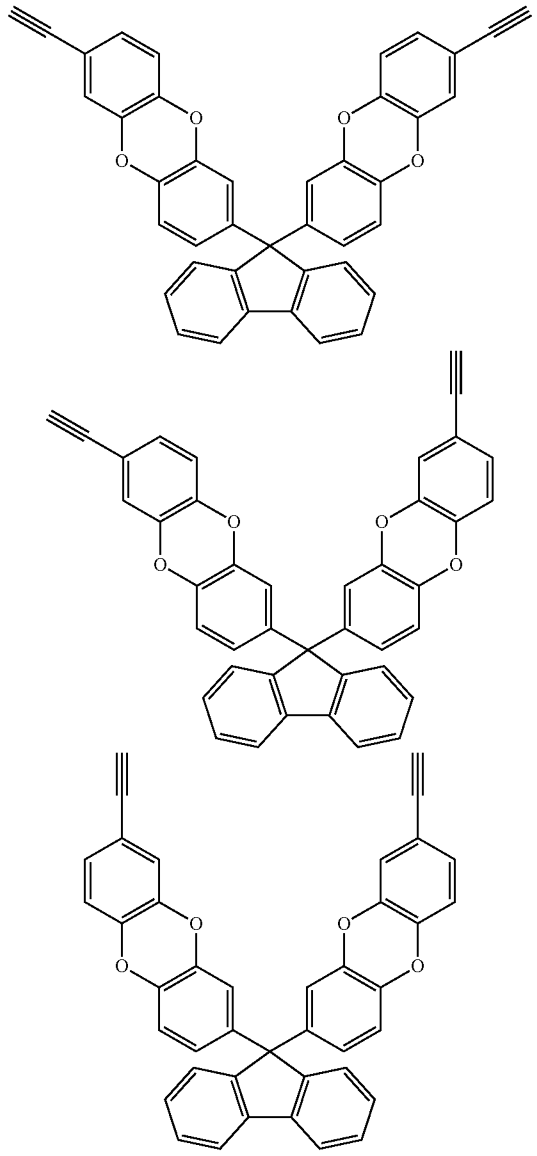

26:49:25

[Synthesis Example 5] Synthesis of Compound (A5)

To 20.0 g of tetraol (B3), 18.1 g of fluorobenzene (C2), and 25.4 g of potassium carbonate, 200 g of N-methylpyrrolidone was added for reaction with an inner temperature of 140° C. for 24 hours under nitrogen atmosphere. After cooling at room temperature, 300 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 300 g of hexane. The precipitated crystal was separated by filtration, washed twice with 200 g of hexane, and collected. The collected crystal was vacuum dried at 70° C. Thus, (A5) was obtained as a mixture shown below. The isomer ratio determined by LC is also shown. Additionally, when the weight-average molecular weight (Mw) and dispersity (Mw/Mn) were measured by GPC, the following results were obtained.

(A5): Mw=720, Mw/Mn=1.05

(A5)

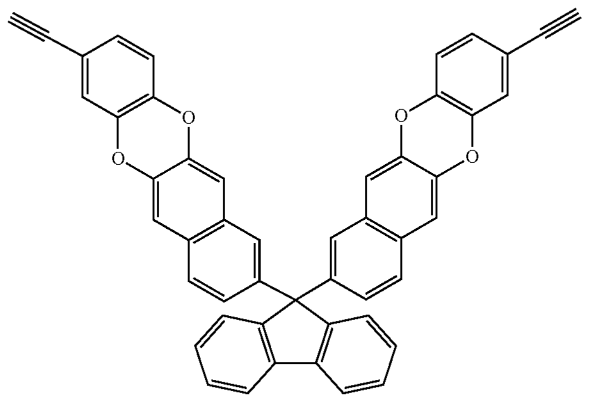

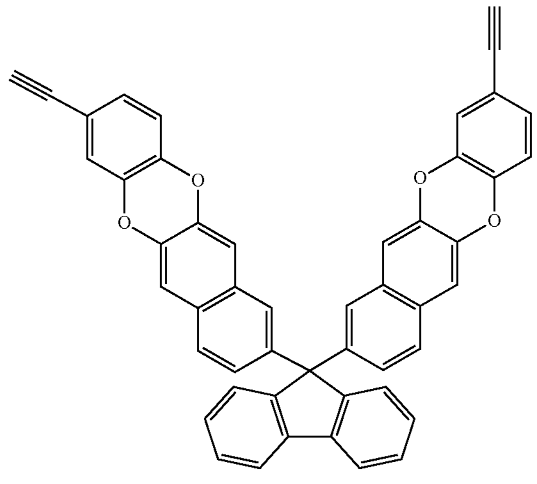

-continued

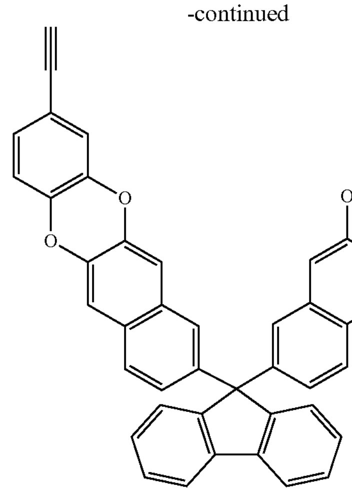

23:50:27

[Synthesis Example 6] Synthesis of Compound (A6)

To 20.0 g of tetraol (B3), 16.2 g of fluorobenzene (C3), and 25.4 g of potassium carbonate, 200 g of N-methylpyrrolidone was added for reaction with an inner temperature of 120° C. for 8 hours under nitrogen atmosphere. After cooling at room temperature, 300 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 400 g of methanol. The precipitated crystal was separated by filtration, washed twice with 300 g of methanol, and collected. The collected crystal was vacuum dried at 70° C. Thus, (A6) was obtained as a mixture shown below. The isomer ratio determined by LC is also shown. Additionally, when the weight-average molecular weight (Mw) and dispersity (Mw/Mn) were measured by GPC, the following results were obtained.

(A6): Mw=760, Mw/Mn=1.04

(A6)

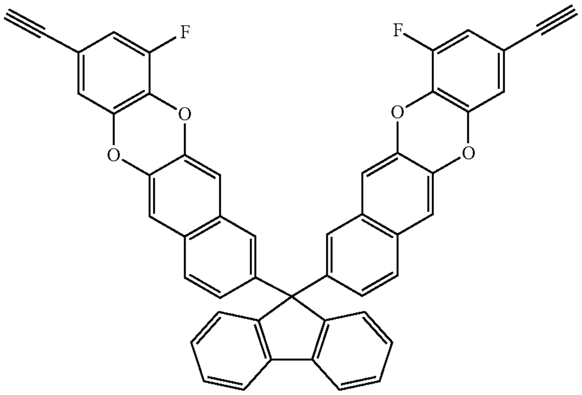

-continued

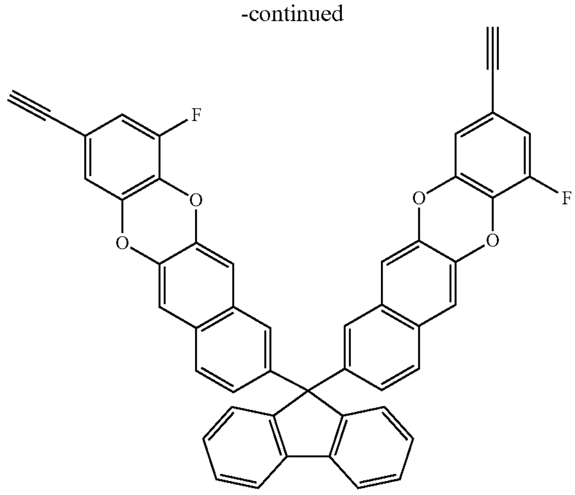

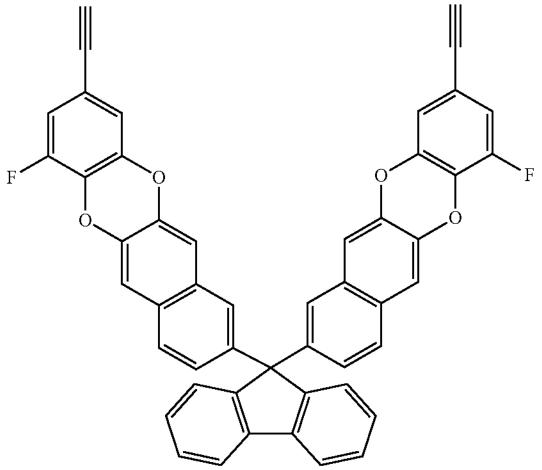

26:48:26

[Synthesis Example 7] Synthesis of Compound (A7)

To 20.0 g of hexol (B4), 25.9 g of fluorobenzene (C2), and 45.4 g of potassium carbonate, 250 g of N-methylpyrrolidone was added for reaction with an inner temperature of 140° C. for 24 hours under nitrogen atmosphere. After cooling at room temperature, 400 ml of methyl isobutyl ketone and 400 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 350 g of methanol. The precipitated crystal was separated by filtration, washed twice with 200 g of methanol, and collected. The collected crystal was vacuum dried at 70° C. Thus, (A7) was obtained as a mixture shown below. The isomer ratio determined by LC is also shown. Additionally, when the weight-average molecular weight (Mw) and dispersity (Mw/Mn) were measured by GPC, the following results were obtained.

(A7): Mw=790, Mw/Mn=1.08

(A7)

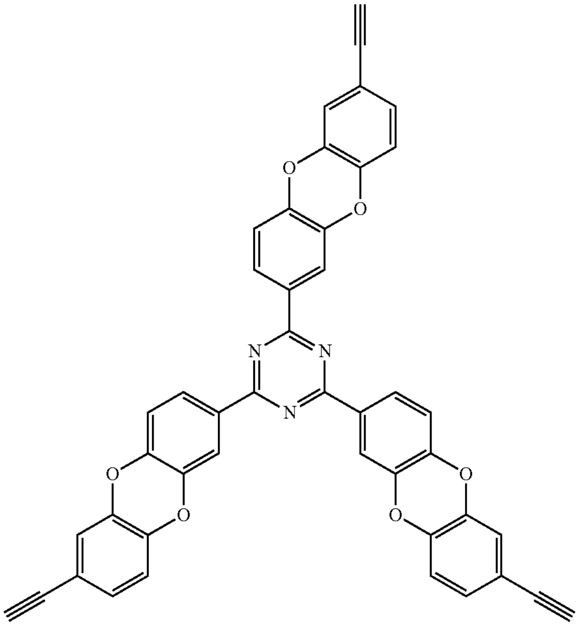

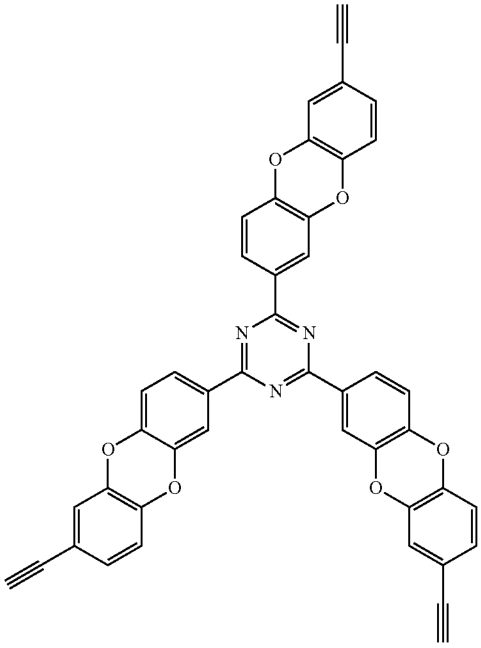

-continued

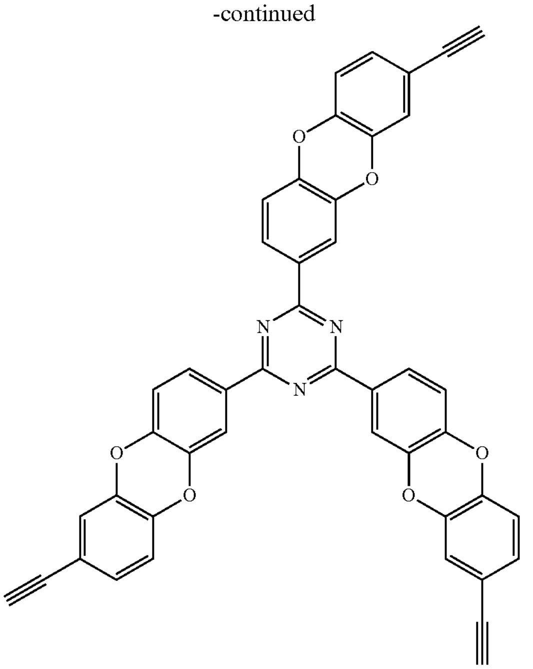

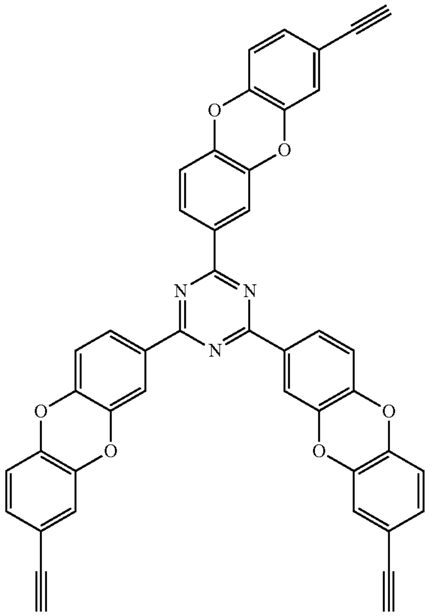

13:37:38:12

[Synthesis Example 8] Synthesis of Compound (R1) for Comparative Examples (R1)

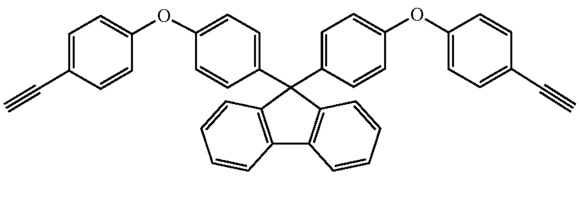

To 20.0 g of the raw material (D1) for synthesis in Comparative Examples, 16.4 g of the raw material (D2) for synthesis in Comparative Examples, and 23.3 g of potassium carbonate, 200 g of N-methylpyrrolidone was added for reaction with an inner temperature of 140° C. for 24 hours under nitrogen atmosphere. After cooling at room temperature, 300 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 350 g of methanol. The precipitated crystal was separated by filtration, washed twice with 200 g of methanol, and collected. The collected crystal was vacuum dried at 70° C. Thus, (R1) was obtained. When the weight-average molecular weight (Mw) and dispersity (Mw/Mn) were measured by GPC, the following results were obtained.

(R1): Mw=580, Mw/Mn=1.03

[Synthesis Example 9] Synthesis of Compound (R2) for Comparative Examples (R2)

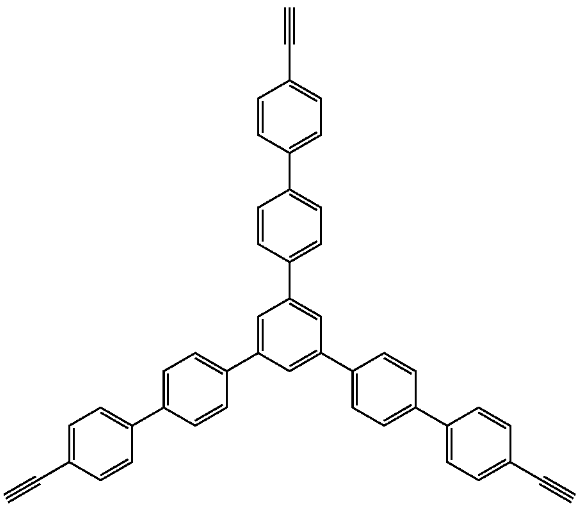

To 20 g of the raw material (D3) for synthesis in Comparative Examples, 8.4 g of trimethylsilylacetylene, 1.0 g of dichlorobis triphenylphosphine palladium(II), 0.4 g of copper(I) iodide, and 20 g of triethylamine, 150 g of THF was added for reaction with an inner temperature of 70° C. for 8 hours under nitrogen atmosphere. After cooling to room temperature, the insoluble matter was separated by filtration, and a crystal was precipitated by adding 300 g of methanol. The obtained crystal was dissolved in 300 ml of ethyl acetate, and the resultant was sequentially washed with 100 ml of a 3% hydrochloric acid aqueous solution, 100 ml of a 3% sodium hydrogen carbonate aqueous solution, and 100 ml of pure water five times. Then, the organic layer was dried under reduced pressure. To the solid dried under reduced pressure, 16.0 g of potassium carbonate, 80 g of THE, and 30 g of methanol were added for reaction at room temperature for 4 hours. After cooling to room temperature, the organic layer was washed twice with 100 ml of a 3% nitric acid aqueous solution and five times with 100 ml of pure water. Then, the organic layer was dried under reduced pressure. To the residue, 60 g of THF was added and a homogeneous solution was formed. Subsequently, a crystal was precipitated with 200 g of methanol. The precipitated crystal was separated by filtration, washed twice with 100 g of methanol, and collected. The collected crystal was vacuum dried at 70° C. Thus, (R2) was obtained. When the weight-average molecular weight (Mw) and dispersity (Mw/Mn) were measured by GPC, the following results were obtained.

(R2): Mw=660, Mw/Mn=1.01

[Synthesis Example 10] Synthesis of Compound (R3) for Comparative Examples (R3)

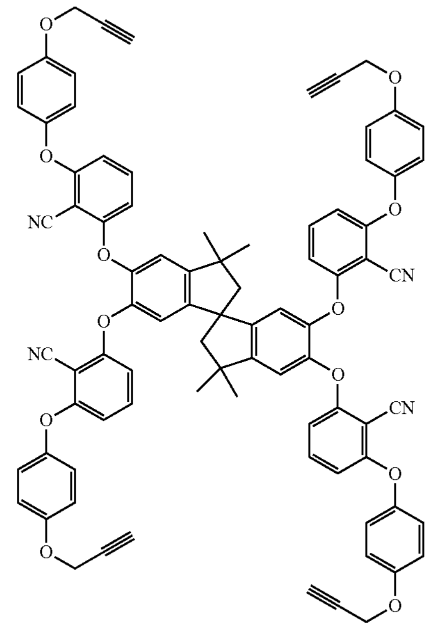

To 10.0 g of the raw material (D4) for synthesis in Comparative Examples, 39.3 g of the raw material (D5) for synthesis in Comparative Examples, and 24.0 g of potassium carbonate, 200 g of N-methylpyrrolidone was added for reaction with an inner temperature of 140° C. for 24 hours under nitrogen atmosphere. After cooling at room temperature, 400 ml of methyl isobutyl ketone and 300 ml of pure water were added to the reaction solution and homogenized. Thereafter, the separated aqueous layer was removed. Further, the organic layer was washed twice with 100 ml of a 3% nitric acid aqueous solution and five times with 100 ml of pure water. Then, the organic layer was dried under reduced pressure. To the residue, 100 g of THF was added and a homogeneous solution was formed. Subsequently, a crystal was precipitated with 400 g of methanol. The precipitated crystal was separated by filtration, washed twice with 300 g of methanol, and collected. The collected crystal was vacuum dried at 70° C. Thus, (R3) was obtained. When the weight-average molecular weight (Mw) and dispersity (Mw/Mn) were measured by GPC, the following results were obtained.

(R3): Mw=1520, Mw/Mn=1.06

[Synthesis Example 11] Synthesis of Compound (R4) for Comparative Examples (R4)

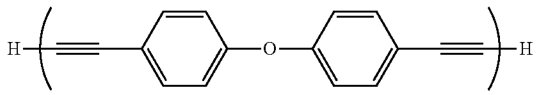

To 30.0 g of the raw material (D6) for synthesis in Comparative Examples, 0.03 g of copper(I) iodide, and 0.20 g of tetramethylethylenediamine, 120 g of toluene was added for reaction with an inner temperature of 50° C. for 3 hours while air bubbles were being generated from an air bubbler. After cooling at room temperature, the resultant was added to a mixture solution containing 20 g of concentrated hydrochloric acid and 500 g of methanol to deposit a crystal. The precipitated crystal was separated by filtration, washed five times with 200 g of methanol, and collected. The collected crystal was vacuum dried at 70° C. Thus, (R4) was obtained. When the weight-average molecular weight (Mw) and dispersity (Mw/Mn) were measured by GPC, the following results were obtained.

(R4): Mw=3100, Mw/Mn=1.85

[Synthesis Example 12] Synthesis of Compound (R5) for Comparative Examples (R5)

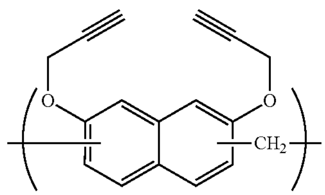

Under nitrogen atmosphere, a homogeneous solution with a liquid temperature of 70° C. was prepared from 80 g of the raw material (D7) for synthesis in Comparative Examples, 22 g of a 37% formalin solution, and 250 g of 1,2-dichloroethane. Then, 5 g of methanesulfonic acid was slowly added thereto, and the reaction was allowed to proceed with the liquid temperature of 80° C. for 12 hours. After cooling to room temperature, 500 ml of MIBK was added to the resultant. After the organic layer was washed five times with 200 g of pure water, the organic layer was dried under reduced pressure. To the residue, 300 g of THF was added and a homogeneous solution was formed. Subsequently, the polymer was reprecipitated with 2000 g of hexane. The precipitated polymer was separated by filtration and dried under reduced pressure. Thus, Compound (R5) was obtained. When the weight-average molecular weight (Mw) and dispersity (Mw/Mn) were measured by GPC, the following results were obtained.

(R5): Mw=3000, Mw/Mn=1.58

The structural formula, weight-average molecular weight (Mw), and dispersity (Mw/Mn) of Compounds (A1) to (A7) obtained as described above are listed in Tables 1 and 2. Additionally, Table 3 shows Compounds (R1) to (R5) used in Comparative Examples, too.

TABLE 1
| Synthesis Example | Compound | Mw | Mw/Mn |
|---|---|---|---|
| 1 | 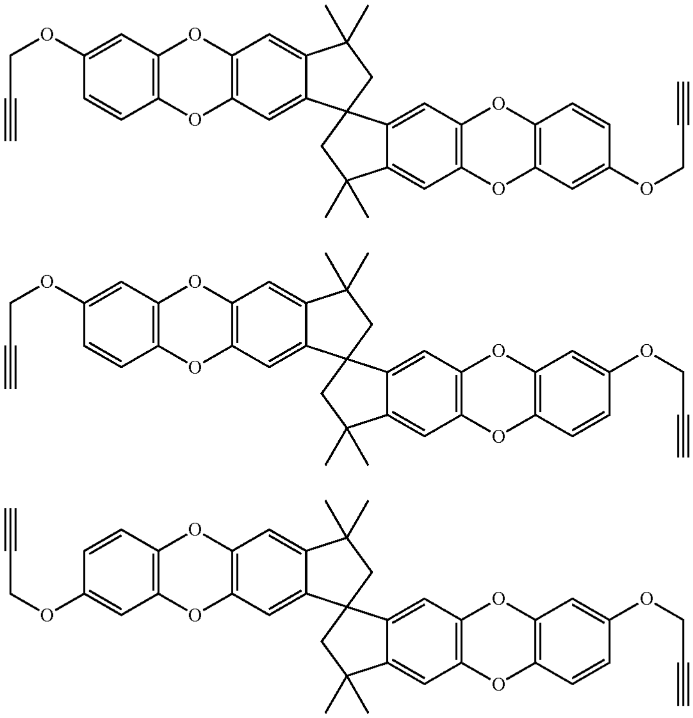 27:45:28 (A 1) | 640 | 1.03 |
| 2 | 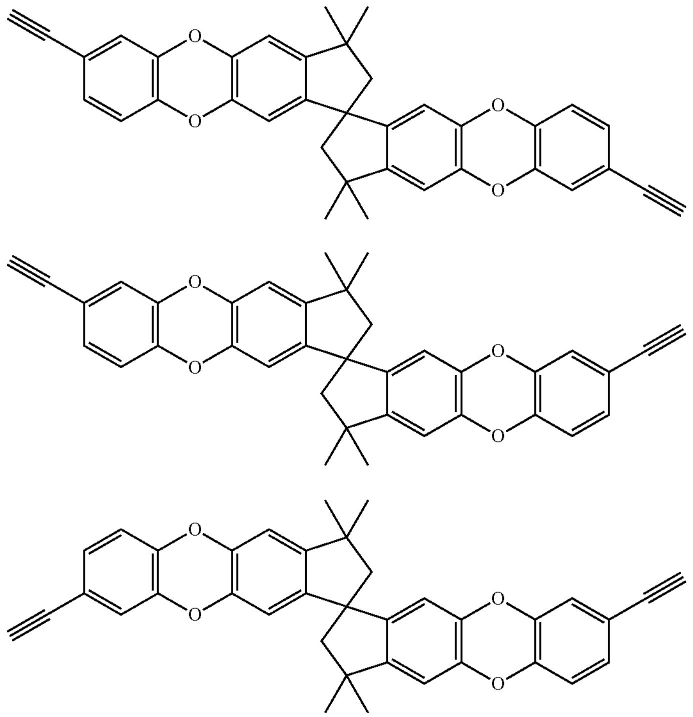 27:46:27 (A 2) | 570 | 1.05 |

TABLE 1-continued
| Synthesis Example | Compound | Mw | Mw/Mn |
|---|---|---|---|
| 3 | 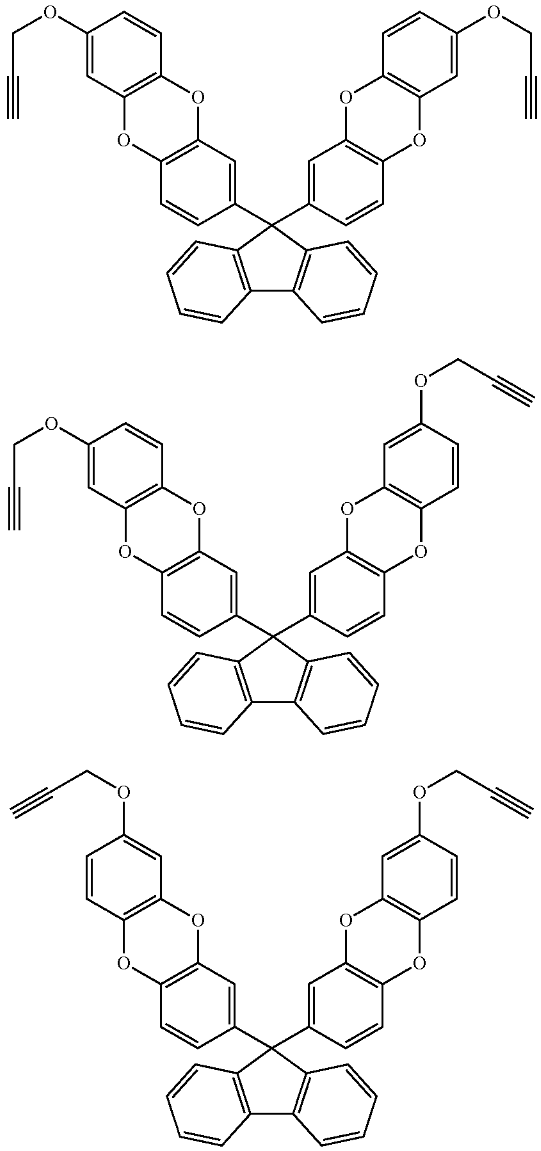 26:48:26 (A 3) | 670 | 1.02 |
| 4 | 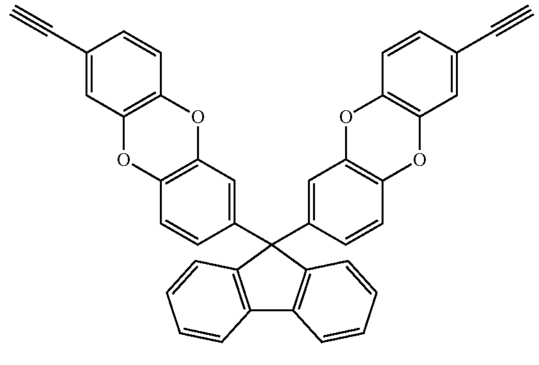 [SMILES: C#Cc1ccc2c(c1)Oc1ccc(C3(c4ccc5c(c4)Oc4ccc(C#C)cc4O5)c4ccccc4-c4ccccc43)cc1O2] | 610 | 1.04 |

TABLE 1-continued
| Synthesis Example | Compound | Mw | Mw/Mn |
|---|---|---|---|
| | 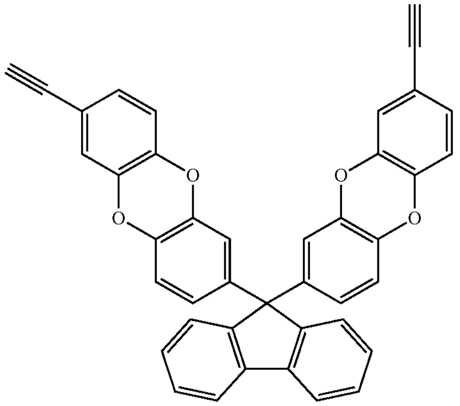 [SMILES: C#Cc1ccc2c(c1)Oc1ccc(C3(c4ccc5c(c4)Oc4cc(C#C)ccc4O5)c4ccccc4-c4ccccc43)cc1O2] 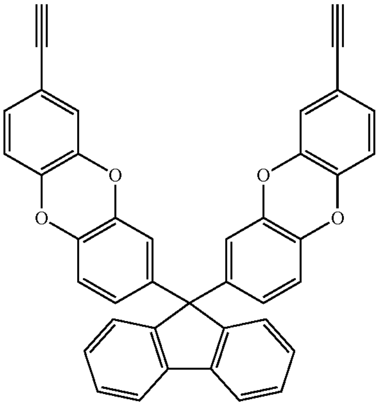 [SMILES: C#Cc1ccc2c(c1)Oc1cc(C3(c4ccc5c(c4)Oc4cc(C#C)ccc4O5)c4ccccc4-c4ccccc43)ccc1O2] 26:49:25 (A 4) | | |
TABLE 2
| Synthesis Example | Compound | Mw | Mw/Mn |
|---|---|---|---|
| 5 | 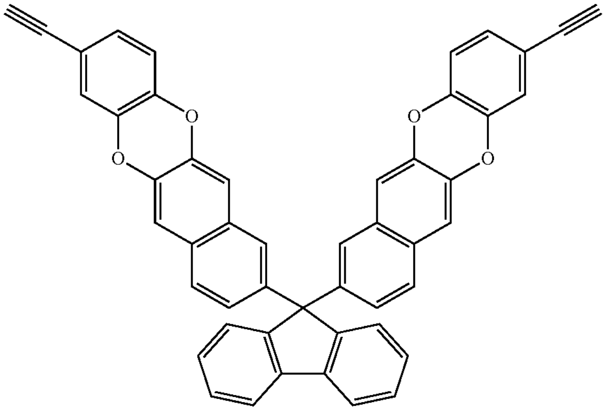 [SMILES: C#Cc1ccc2c(c1)Oc1cc3ccc(C4(c5ccc6cc7c(cc6c5)Oc5ccc(C#C)cc5O7)c5ccccc5-c5ccccc54)cc3cc1O2] | 720 | 1.05 |

TABLE 2-continued
| Synthesis Example | Compound | Mw | Mw/ Mn |
| --- | --- | --- | --- |
| | 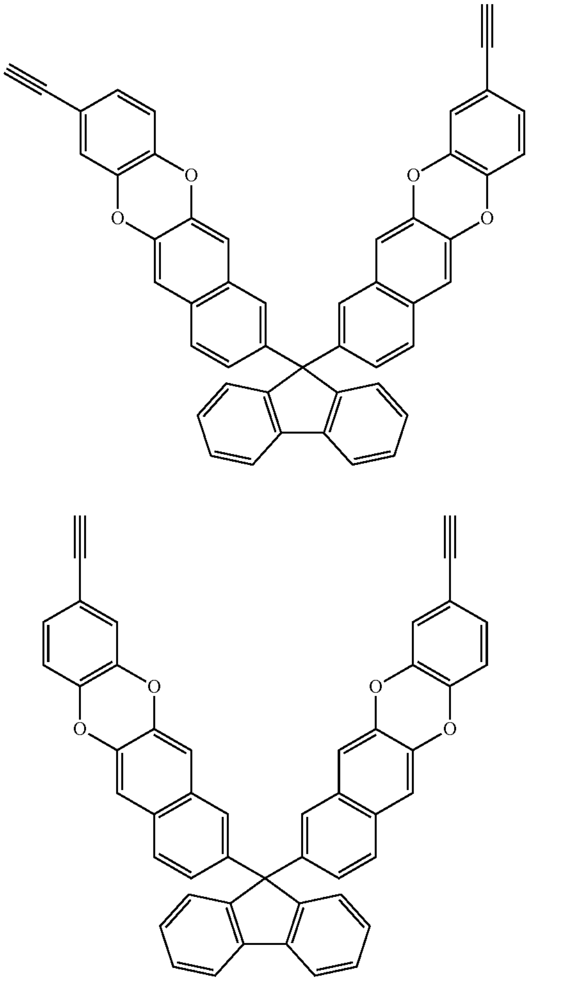 23:50:27 (A 5) | | |
| 6 | 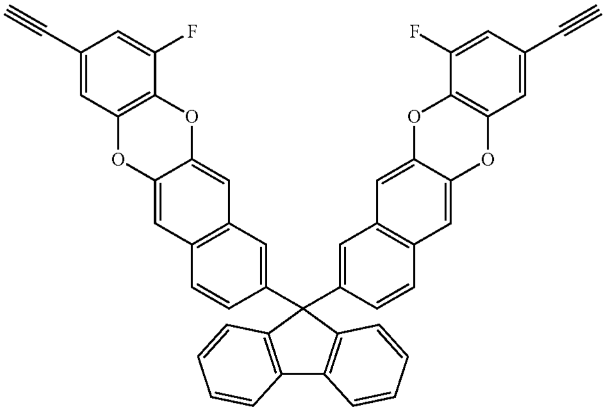 [SMILES: C#Cc1cc(F)c2c(c1)Oc1cc3ccc(C4(c5ccc6cc7c(cc6c5)Oc5c(F)cc(C#C)cc5O7)c5ccccc5-c5ccccc54)cc3cc1O2] | 760 | 1.04 |

TABLE 2-continued
| Synthesis Example | Compound | Mw | Mw/ Mn |
|---|---|---|---|
| | 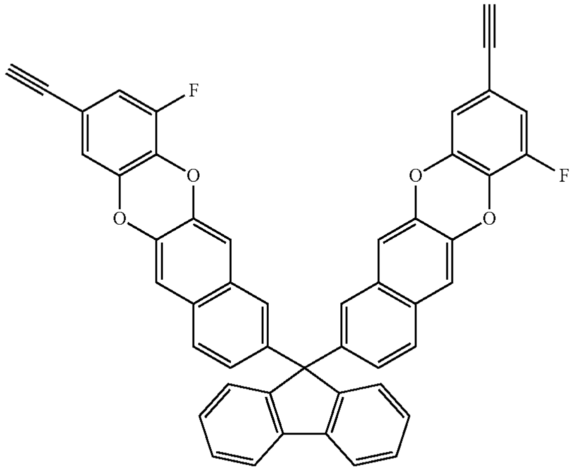 [SMILES: C#Cc1cc(F)c2c(c1)Oc1cc3cc(C4(c5ccc6cc7c(cc6c5)Oc5c(F)cc(C#C)cc5O7)c5ccccc5-c5ccccc54)ccc3cc1O2] 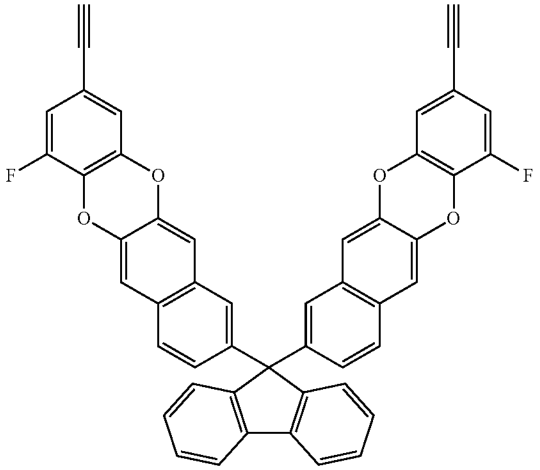 [SMILES: C#Cc1cc(F)c2c(c1)Oc1cc3cc(C4(c5ccc6cc7c(cc6c5)Oc5cc(C#C)cc(F)c5O7)c5ccccc5-c5ccccc54)ccc3cc1O2] 26:48:26 (A 6) | | |
| 7 | 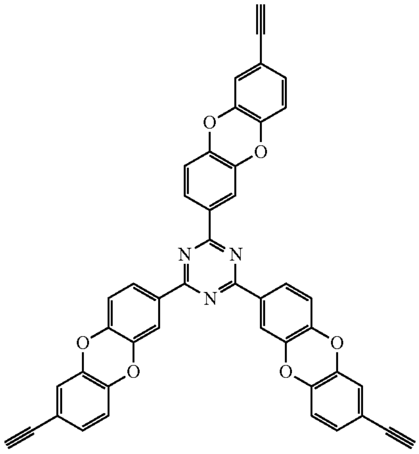 [SMILES: C#Cc1ccc2c(c1)Oc1ccc(-c3nc(-c4ccc5c(c4)Oc4ccc(C#C)cc4O5)nc(-c4ccc5c(c4)Oc4ccc(C#C)cc4O5)n3)cc1O2] | 790 | 1.08 |

TABLE 2-continued
| Synthesis Example | Compound | Mw | Mw/Mn |
|---|---|---|---|
| | 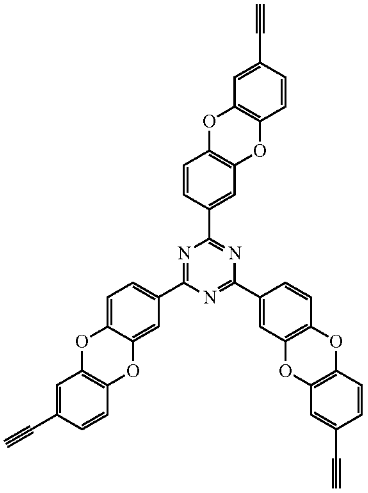 [SMILES: C#Cc1ccc2c(c1)Oc1ccc(-c3nc(-c4ccc5c(c4)Oc4ccc(C#C)cc4O5)nc(-c4ccc5c(c4)Oc4cc(C#C)ccc4O5)n3)cc1O2] | | |
| | 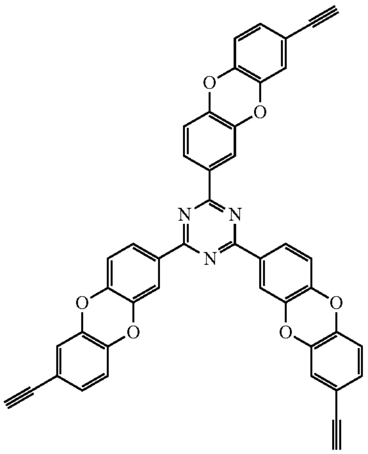 [SMILES: C#Cc1ccc2c(c1)Oc1ccc(-c3nc(-c4ccc5c(c4)Oc4cc(C#C)ccc4O5)nc(-c4ccc5c(c4)Oc4cc(C#C)ccc4O5)n3)cc1O2] | | |
| | 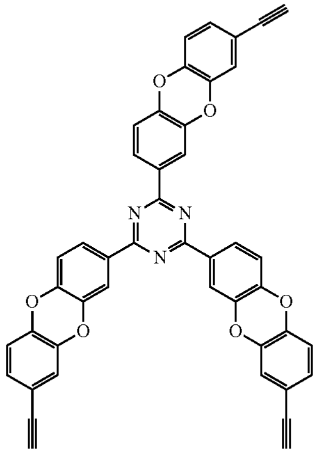 [SMILES: C#Cc1ccc2c(c1)Oc1cc(-c3nc(-c4ccc5c(c4)Oc4cc(C#C)ccc4O5)nc(-c4ccc5c(c4)Oc4cc(C#C)ccc4O5)n3)ccc1O2]<br>13:37:38:12<br>(A 7) | | |

TABLE 3
| Synthesis Example | Compound | Mw | Mw/ Mn |
|---|---|---|---|
| 8 | 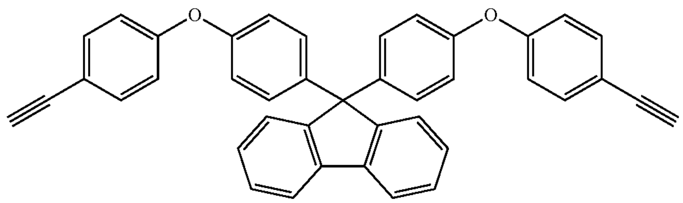 [SMILES: C#Cc1ccc(Oc2ccc(C3(c4ccc(Oc5ccc(C#C)cc5)cc4)c4ccccc4-c4ccccc43)cc2)cc1]<br>(R 1 ) | 580 | 1.03 |
| 9 | 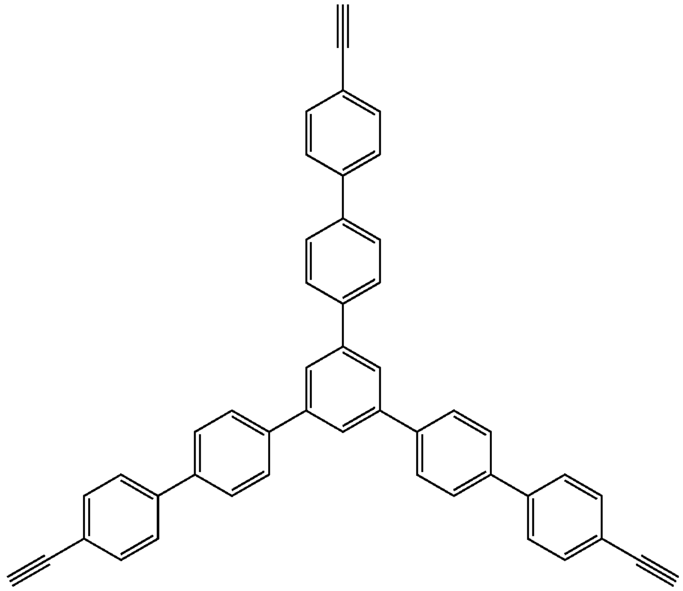 [SMILES: C#Cc1ccc(-c2ccc(-c3cc(-c4ccc(-c5ccc(C#C)cc5)cc4)cc(-c4ccc(-c5ccc(C#C)cc5)cc4)c3)cc2)cc1]<br>(R 2) | 660 | 1.01 |
| 10 | 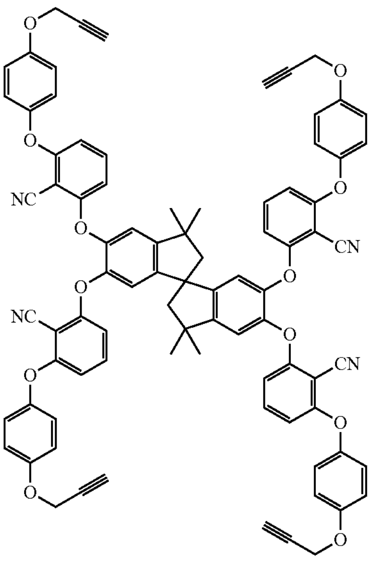 [SMILES: C#CCOc1ccc(Oc2cccc(Oc3cc4c(cc3Oc3cccc(Oc5ccc(OCC#C)cc5)c3C#N)C3(CC4(C)C)CC(C)(C)c4cc(Oc5cccc(Oc6ccc(OCC#C)cc6)c5C#N)c(Oc5cccc(Oc6ccc(OCC#C)cc6)c5C#N)cc43)c2C#N)cc1]<br>(R 3) | 1520 | 1.06 |
| 11 | 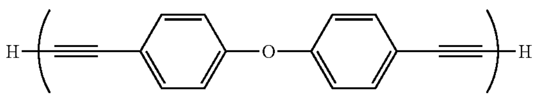 | 3100 | 1.85 |

TABLE 3-continued

| Synthesis Example | Compound | Mw | Mw/Mn |
|---|---|---|---|
| 12 | (R 4) 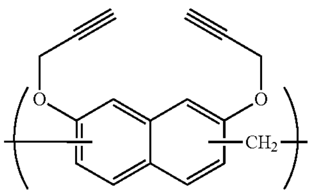 (R 5) | 3000 | 1.58 |

Preparation of Materials (UDL-1 to -9, Comparative UDL-1 to -5) for forming Organic Film According to proportions shown in Table 4, Compounds (A1) to (A7) and (R1) to (R5) were dissolved in solvents containing propylene glycol monomethyl ether acetate (PGMEA) or cyclohexanone (CyHO), 0.1 mass % FC-4430 (manufactured by Sumitomo 3M Ltd.) and optionally a high-boiling-point solvent of (S1) 1,6-diacetoxyhexane: boiling point of 260° C. or (S2) tripropylene glycol monomethyl ether: boiling point of 242° C. The resulting solutions were filtered through a 0.1-μm filter made of a fluorinated resin. Thus, materials (UDL-1 to -9, Comparative UDL-1 to -5) for forming an organic film were prepared.

TABLE 4

| Material for forming organic film | Compound (parts by mass) | High-boiling-point solvent (parts by mass) | CYHO (parts by mass) | PGMEA (parts by mass) |
|---|---|---|---|---|
| UDL-1 | A1 (10) | — | — | 90 |
| UDL-2 | A2 (10) | — | — | 90 |
| UDL-3 | A3 (10) | — | — | 90 |
| UDL-4 | A4 (10) | — | — | 90 |
| UDL-5 | A5 (10) | — | — | 90 |
| UDL-6 | A6 (10) | — | — | 90 |
| UDL-7 | A7 (10) | — | — | 90 |
| UDL-8 | A2 (10) | S1 (10) | — | 80 |
| UDL-9 | A5 (10) | S2 (10) | — | 80 |
| Comparative UDL-1 | R1 (10) | — | — | 90 |
| Comparative UDL-2 | R2 (10) | — | 90 | — |
| Comparative UDL-3 | R3 (10) | — | — | 90 |
| Comparative UDL-4 | R4 (10) | — | 90 | — |
| Comparative UDL-5 | R5 (10) | — | — | 90 |

Example 1: Solvent Resistance Measurement (Examples 1-1 to 1-9, Comparative Examples 1-1 to 1-5)

A silicon substrate was coated with one of the materials (UDL-1 to -9, comparative UDL-1 to -5) for forming an organic film prepared above and baked at 450° C. for 60 seconds under such a nitrogen stream that the oxygen concentration was controlled to 0.2% or less. Then, the film thickness was measured. A PGMEA solvent was dispensed on each film and allowed to stand for 30 seconds. The resultant was spin-dried and baked at 100° C. for 60 seconds to evaporate the PGMEA, and the film thickness was measured. A difference in film thicknesses before and after the PGMEA treatment was determined. Table 5 shows these results.

TABLE 5

| | Material for forming organic film | Film thickness after film formation: a (Å) | Film thickness after PGMEA treatment: b (Å) | b/a × 100 (%) |
|---|---|---|---|---|
| Example 1-1 | UDL-1 | 2003 | 2001 | 99.9 |
| Example 1-2 | UDL-2 | 2002 | 2001 | 100.0 |
| Example 1-3 | UDL-3 | 2004 | 2002 | 99.9 |
| Example 1-4 | UDL-4 | 2003 | 2002 | 100.0 |
| Example 1-5 | UDL-5 | 2001 | 2000 | 100.0 |
| Example 1-6 | UDL-6 | 1996 | 1994 | 99.9 |
| Example 1-7 | UDL-7 | 1998 | 1995 | 99.8 |
| Example 1-8 | UDL-8 | 1997 | 1995 | 99.9 |
| Example 1-9 | UDL-9 | 2003 | 2000 | 99.9 |
| Comparative Example 1-1 | Comparative UDL-1 | 1998 | 1978 | 99.0 |
| Comparative Example 1-2 | Comparative UDL-2 | 2000 | 1998 | 99.9 |
| Comparative Example 1-3 | Comparative UDL-3 | 2003 | 1700 | 84.9 |
| Comparative Example 1-4 | Comparative UDL-4 | 2007 | 1994 | 99.4 |
| Comparative Example 1-5 | Comparative UDL-5 | 1997 | 1597 | 80.0 |

As shown in Table 5, the inventive materials for forming an organic film (Examples 1-1 to 1-9) after the PGMEA treatment resulted in the film remaining percentages of 99.8% or more. This indicates that the crosslinking reaction took place even under the nitrogen atmosphere, and sufficient solvent resistance was exhibited. In contrast, in Comparative Examples 1-1 and 1-3 to 1-5 with ether structure, the film remaining percentages after the PGMEA treatment were less than 99.5% due to insufficient heat resistance. Particularly, the film remaining percentages of Comparative Examples 1-3 and 1-5 were less than 90%. In Comparative Example 1-2 without ether structure, solvent resistance was exhibited and the film remaining percentage was not less than 99.8%. These results indicate that the dioxin rings contain heteroatoms but result in excellent heat resistance because of the heterocyclic structure formation, unlike ether structure.

Example 2: Heat Resistance Evaluation (Examples 2-1 to 2-9, Comparative Examples 2-1 to 2-5)

A silicon substrate was coated with one of the materials (UDL-1 to -9, Comparative UDL-1 to -5) for forming an organic film and baked in the atmosphere at 180° C. to form a coating film of 200 nm. The film thickness was measured. This substrate was further baked at 450° C. for 10 minutes under such a nitrogen stream that the oxygen concentration was controlled to 0.2% or less. Then, the film thickness was measured. The results are shown in Table 6.

TABLE 6

| | Material for forming organic film | Film thickness at 180° C.: A (Å) | Film thickness at 450° C.: B (Å) | Film remaining percentage: % (B/A) |
|---|---|---|---|---|
| Example 2-1 | UDL-1 | 2005 | 1958 | 97.6 |
| Example 2-2 | UDL-2 | 2002 | 1999 | 99.9 |
| Example 2-3 | UDL-3 | 2004 | 1955 | 97.6 |
| Example 2-4 | UDL-4 | 2009 | 1996 | 99.4 |
| Example 2-5 | UDL-5 | 2000 | 1982 | 99.1 |
| Example 2-6 | UDL-6 | 2009 | 1992 | 99.2 |
| Example 2-7 | UDL-7 | 2000 | 1990 | 99.5 |
| Example 2-8 | UDL-8 | 2007 | 1989 | 99.1 |
| Example 2-9 | UDL-9 | 2003 | 1992 | 99.5 |
| Comparative Example 2-1 | Comparative UDL-1 | 1998 | 1179 | 59.0 |
| Comparative Example 2-2 | Comparative UDL-2 | 2006 | 2001 | 99.7 |
| Comparative Example 2-3 | Comparative UDL-3 | 2007 | 1071 | 53.4 |
| Comparative Example 2-4 | Comparative UDL-4 | 2007 | 905 | 45.1 |
| Comparative Example 2-5 | Comparative UDL-5 | 2002 | 664 | 33.2 |

As shown in Table 6, in the inventive materials for forming an organic film (Examples 2-1 to 2-9), the film thicknesses were decreased by less than 3% even after the baking at 450° C. for 10 minutes. The inventive materials for forming an organic film make it possible to form organic films having high heat resistance even under high-temperature conditions of 450° C. In particular, in Examples 2-2, 2-4, 2-5, 2-6, 2-7, 2-8, and 2-9 with ethynyl groups as $R_1$, the decrease in the film thicknesses was suppressed to less than 1% even after the baking at 450° C. for 10 minutes. This shows that heat resistance is particularly excellent. In contrast, in Comparative Examples 2-1, 2-3, 2-4, and 2-5 with ether bonds, the film thicknesses were greatly decreased by more than 40%. This suggests that, although the dioxin rings containing heteroatoms, high heat resistance was exhibited as in the results of Example 1.

Example 3: Filling Property Evaluation (Examples 3-1 to 3-9, Comparative Examples 3-1 to 3-5)

As shown in FIG. 3, the materials (UDL-1 to -9, comparative UDL-1 to -5) for forming an organic film were respectively applied onto $SiO_2$ wafer substrates each having a dense hole pattern (hole diameter: 0.16 μm, hole depth: 0.50 μm, distance between the centers of two adjacent holes: 0.32 μm) and baked with a hot plate at 450° C. for 600 seconds under such a nitrogen stream that the oxygen concentration was controlled to 0.2% or less. In this manner, organic films 8 were formed. The substrates thus used were base substrates 7 ($SiO_2$ wafer substrates) each having a dense hole pattern as shown in FIG. 3 (G) (top view) and (H) (sectional view). The sectional shapes of the resulting wafer substrates were observed with a scanning electron microscope (SEM) to check whether or not the holes were filled with the organic film 8 without voids (space). Table 7 shows the results. If an organic film material having poor filling property is used, voids occur inside the holes in this evaluation. If an organic film material having good filling property is used, the holes are filled with the organic film 8 without voids in this evaluation as shown in FIG. 3 (I).

TABLE 7

| | Material for forming organic film | Presence/absence of voids |
|---|---|---|
| Example 3-1 | UDL-1 | absent |
| Example 3-2 | UDL-2 | absent |
| Example 3-3 | UDL-3 | absent |
| Example 3-4 | UDL-4 | absent |
| Example 3-5 | UDL-5 | absent |
| Example 3-6 | UDL-6 | absent |
| Example 3-7 | UDL-7 | absent |
| Example 3-8 | UDL-8 | absent |
| Example 3-9 | UDL-9 | absent |
| Comparative Example 3-1 | Comparative UDL-1 | present |
| Comparative Example 3-2 | Comparative UDL-2 | absent |
| Comparative Example 3-3 | Comparative UDL-3 | present |
| Comparative Example 3-4 | Comparative UDL-4 | present |
| Comparative Example 3-5 | Comparative UDL-5 | present |

As shown in Table 7, it was verified that the inventive materials for forming an organic film (Examples 3-1 to 3-9) enabled the hole patterns to be filled without voids, and that the filling property was favorable. Meanwhile, in Comparative Examples 3-1, 3-3, 3-4, and 3-5, voids caused by insufficient heat resistance had occurred in accordance with the results of Example 2. From these results, it was confirmed that the inventive materials for forming an organic film had favorable filling property.

Example 4: Planarizing Property Evaluation (Examples 4-1 to 4-9, Comparative Examples 4-1 to 4-5)

The materials (UDL-1 to -9, Comparative UDL-1 to -5) for forming an organic film were respectively applied onto base substrates 9 ($SiO_2$ wafer substrates) each having a giant isolated trench pattern (FIG. 4 (J), trench width: 10 μm, trench depth: 0.10 μm), and baked at 450° C. for 60 seconds under such a nitrogen stream that the oxygen concentration was controlled to 0.2% or less. In this manner, organic films 10 were formed. Then, a step delta 10 (FIG. 4 (K)) between the trench portion and the non-trench portion of each organic film 10 was observed with an atomic force microscope (AFM) NX10 manufactured by Park systems Corp. Table 8 shows the results. In this evaluation, the smaller the step, the better the planarizing property. Note that, in this evaluation, a trench pattern having a depth of 0.10 μm was planarized using an organic film material generally having a film thickness of approximately 0.2 μm. This is a severe evaluation condition to evaluate the planarizing property.

TABLE 8

| | Material for forming organic film | Step (nm) |
|---|---|---|
| Example 4-1 | UDL-1 | 30 |
| Example 4-2 | UDL-2 | 20 |
| Example 4-3 | UDL-3 | 25 |
| Example 4-4 | UDL-4 | 20 |
| Example 4-5 | UDL-5 | 25 |
| Example 4-6 | UDL-6 | 25 |
| Example 4-7 | UDL-7 | 30 |
| Example 4-8 | UDL-8 | 10 |
| Example 4-9 | UDL-9 | 15 |
| Comparative Example 4-1 | Comparative UDL-1 | 40 |
| Comparative Example 4-2 | Comparative UDL-2 | 90 |
| Comparative Example 4-3 | Comparative UDL-3 | 45 |
| Comparative Example 4-4 | Comparative UDL-4 | 40 |
| Comparative Example 4-5 | Comparative UDL-5 | 85 |

As shown in Table 8, it was verified that the inventive materials for forming an organic film (Examples 4-1 to 4-9) resulted in the organic films which had smaller steps between the trench and non-trench portions than those in Comparative Examples 4-1 to 4-5, and that the planarizing property was excellent. In Comparative Examples 4-1, 4-3, and 4-4, relatively favorable planarizing property was exhibited since flowability was imparted by the ether bonds; however, heat resistance was insufficient, as shown by the results of the heat resistance evaluation in Example 2, and the films shrank considerably by the baking at 450° C., resulting in poor flatness. Meanwhile, in Comparative Example 4-2, the ethynyl groups served as crosslinking groups, so that heat resistance was excellent; however, since there was no dioxane ring structure unlike the present invention, the flowability was not improved, resulting in poor flatness. Furthermore, the comparison of Examples 4-8 and 4-9 in which the high-boiling-point solvent was added with Examples 4-2 and 4-5 in which the high-boiling-point solvent was not added revealed that adding the high-boiling-point solvent further improves planarizing property. From these results, it is revealed that the inventive materials for forming an organic film suppress film shrinking during high-temperature baking because of the excellent heat resistance, and exhibit excellent planarizing property.

Example 5: Patterning Test (Examples 5-1 to 5-9, Comparative Example 5-1

The materials (UDL-1 to -9, comparative UDL-2) for forming an organic film were respectively applied onto silicon wafer substrates on each of which a $SiO_2$ film of 300 nm had been formed. Then, the resultant was baked at 450° C. for 60 seconds under such a nitrogen stream that the oxygen concentration was controlled to 0.2% or less. Thereby, an organic film (resist underlayer film) was formed. A CVD-SiON hard mask was formed thereon, and further, an organic antireflective coating material (ARC-29A: manufactured by Nissan Chemical Industries, Ltd.) was applied and baked at 210° C. for 60 seconds to form an organic antireflective coating having a film thickness of 80 nm. A monolayer resist for ArF was applied thereon as a resist upper layer film material and baked at 105° C. for 60 seconds to form a photoresist film having a film thickness of 100 nm. A liquid immersion top coat material (TC-1) was applied on the photoresist film and baked at 90° C. for 60 seconds to form a top coat having a film thickness of 50 nm. Note that regarding Comparative UDL-1 and UDL-3 to UDL-5, it was not possible to form a CVD-SiON hard mask due to poor heat resistance as in the results of Example 2, and therefore, the subsequent patterning test was unable to proceed.

The resist upper layer film material (monolayer resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 9; and filtering the solution through a 0.1-μm filter made of a fluorinated resin.

TABLE 9

| | Polymer (parts by mass) | Acid generator (parts by mass) | Basic compound (parts by mass) | Solvent (parts by mass) |
|---|---|---|---|---|
| Monolayer resist for ArF | RP1 (100) | PAG1 (6.6) | Amine1 (0.8) | PGMEA (2500) |

The polymer (RP1), acid generator (PAG1), and basic compound (Amine1) used are shown below.

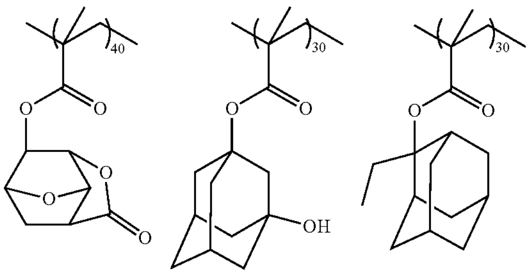

RP1
Mw7,800

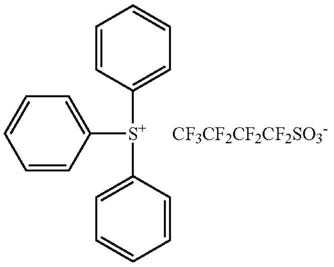

PAG1

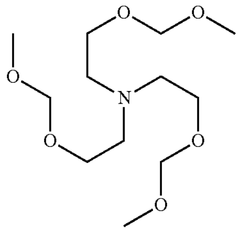

Amine1

The liquid immersion top coat material (TC-1) was prepared by: dissolving a top coat polymer (PP1) into organic solvents in proportions shown in Table 10; and filtering the solution through a 0.1-μm filter made of a fluorinated resin.

TABLE 10

| | Polymer (parts by mass) | Organic solvent (parts by mass) |
|---|---|---|
| TC-1 | PP1 (100) | diisoamyl ether (2700)<br>2-methyl-1-butanol (270) |

The polymer (PP1) used is shown below.

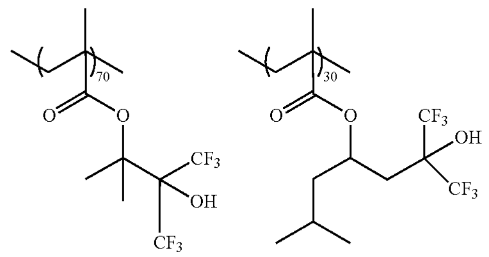

PP1
Mw8,8000

Next, the resulting substrate was exposed to light with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked at 100° C. for 60 seconds (PEB), and developed with a 2.38 mass % tetramethylammonium hydroxide (TMAH) aqueous solution for 30 seconds. Thus, a 55 nm 1:1 positive line and space pattern was obtained.

Next, the organic antireflective coating and the CVD-SiON hard mask were processed by dry etching while using the resist pattern as a mask with an etching apparatus Telius manufactured by Tokyo Electron Limited to form a hard mask pattern. The organic film was etched while using the obtained hard mask pattern as a mask to form an organic film pattern. The $SiO_2$ film was processed by etching while using the obtained organic film pattern as a mask. The etching conditions were as follows.

Conditions for transferring the resist pattern to the SiON hard mask.

Chamber pressure: 10.0 Pa
RF power: 1,500 W
$CF_4$ gas flow rate: 75 sccm
$O_2$ gas flow rate: 15 sccm
Time: 15 sec Conditions for transferring the hard mask pattern to the organic film.

Chamber pressure: 2.0 Pa
RF power: 500 W
Ar gas flow rate: 75 sccm
$O_2$ gas flow rate: 45 sccm
Time: 120 sec Conditions for transferring the organic film pattern to the $SiO_2$ film.

Chamber pressure: 2.0 Pa
RF power: 2,200 W
$C_5F_{12}$ gas flow rate: 20 sccm
$C_2F_6$ gas flow rate: 10 sccm
Ar gas flow rate: 300 sccm
$O_2$ gas flow rate: 60 sccm
Time: 90 sec The pattern cross sections were observed with an electron microscope (S-4700) manufactured by Hitachi, Ltd. Table 11 shows the results.

TABLE 11

| | Material for forming organic film | Pattern profile after etching for transferring to substrate |
|---|---|---|
| Example 5-1 | UDL-1 | Vertical profile |
| Example 5-2 | UDL-2 | Vertical profile |
| Example 5-3 | UDL-3 | Vertical profile |
| Example 5-4 | UDL-4 | Vertical profile |
| Example 5-5 | UDL-5 | Vertical profile |
| Example 5-6 | UDL-6 | Vertical profile |
| Example 5-7 | UDL-7 | Vertical profile |
| Example 5-8 | UDL-8 | Vertical profile |
| Example 5-9 | UDL-9 | Vertical profile |
| Comparative Example 5-1 | Comparative UDL-2 | Pattern collapse |

TABLE 11-continued

As shown from the results of the inventive materials for forming an organic film (Examples 5-1 to 5-9) in Table 11, the resist upper layer film patterns were favorably transferred to the final substrates in all the cases. This confirms that the inventive materials for forming an organic film are suitably used in fine processing according to the multilayer resist method. In Comparative Example 5-1, a CVD-SiON hard mask was formed on the underlayer film (organic film), but the film peeled off from the substrate in forming a pattern due to insufficient adhesiveness of the film. Therefore, it was not possible to form a pattern.

Example 6: Adhesiveness Test (Examples 6-1 to 6-9, Comparative Example 6-1

The materials (UDL-1 to -9, comparative UDL-2) for forming an organic film were respectively applied onto $SiO_2$ wafer substrates and baked at 450° C. for 60 seconds under such a nitrogen stream that the oxygen concentration was controlled to 0.2% or less. Thus, organic films each with a film thickness of 200 nm were formed. This wafer with an organic film was cut into a 1×1 cm square, and an aluminum pin with epoxy adhesive was fastened to the cut wafer with a dedicated jig. Thereafter, the assembly was heated with an oven at 150° C. for 1 hour to bond the aluminum pin to the substrate. After cooling to room temperature, initial adhesiveness was evaluated based on the resistance force by a thin-film adhesion strength measurement apparatus (Sebastian Five-A).

FIG. 5 shows an explanatory diagram showing the adhesiveness measurement method. In FIG. 5, reference number 11 denotes a silicon wafer (substrate), 12 denotes an organic film, 13 denotes an aluminum pin with adhesive, 14 denotes a support, 15 denotes a grip, and 16 denotes a tensile direction. Each adhesive force is an average of 12 measurement points, and a larger value indicates that the organic film has higher adhesiveness with respect to the substrate. The adhesiveness was evaluated by comparing the obtained values. Table 12 shows the results.

TABLE 12

| | Material for forming organic film | Adhesive force (mN) |
|---|---|---|
| Example 6-1 | UDL-1 | 590 |
| Example 6-2 | UDL-2 | 590 |
| Example 6-3 | UDL-3 | 570 |
| Example 6-4 | UDL-4 | 560 |
| Example 6-5 | UDL-5 | 540 |
| Example 6-6 | UDL-6 | 530 |
| Example 6-7 | UDL-7 | 550 |

TABLE 12-continued

| | Material for forming organic film | Adhesive force (mN) |
|---|---|---|
| Example 6-8 | UDL-8 | 520 |
| Example 6-9 | UDL-9 | 560 |
| Comparative Example 6-1 | Comparative UDL-2 | 10 |

As shown in Table 12, it can be seen that the materials for forming an organic film (Examples 6-1 to 6-9), which contain the inventive compounds having dioxin rings for forming an organic film, were superior in adhesive force to Comparative Example 6-1, where it was impossible to form a pattern in the patterning test result of Example 5. The results of the adhesive force test also confirmed that the inventive materials for forming an organic film are suitably used as pattern formation materials.

From the above, it was revealed that the inventive materials for forming an organic film containing the inventive compound for forming an organic film have heat resistance to 400° C. or higher and high filling/planarizing properties even in an oxygen-free inert gas. Thus, the inventive materials for forming an organic film are quite useful as organic film materials used in multilayer resist methods. Moreover, the inventive patterning processes using the materials can precisely form a fine pattern even when a substrate to be processed is a substrate with step.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A material for forming an organic film, comprising:

(A) a compound for forming an organic film shown by the following general formula (1C), (1D) or (1E); and (B) an organic solvent, (1C)

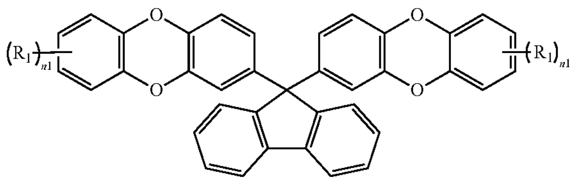

(1D)

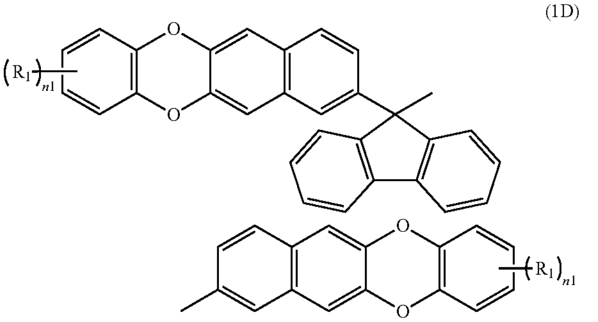

(1E)

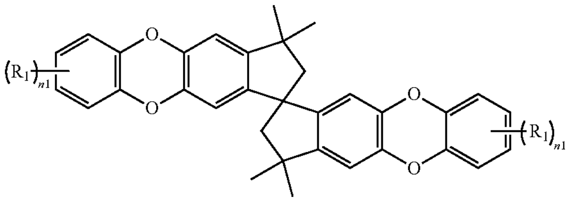

wherein n1 represents an integer of 1 or 2, and a hydrogen atom of a benzene ring in the formula (1C), (1D) or (1E) is optionally substituted with a fluorine atom,

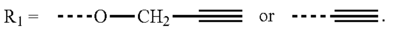

2. The material for forming an organic film according to claim 1, wherein the component (A) is a compound shown by the following formula (1F), (1G), or (1H), (1F)

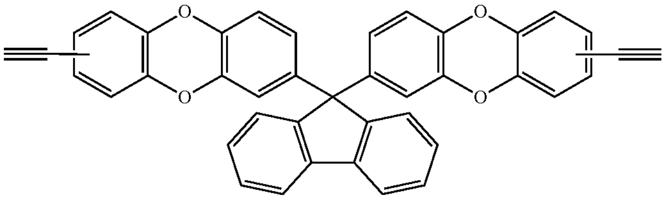

(1G)

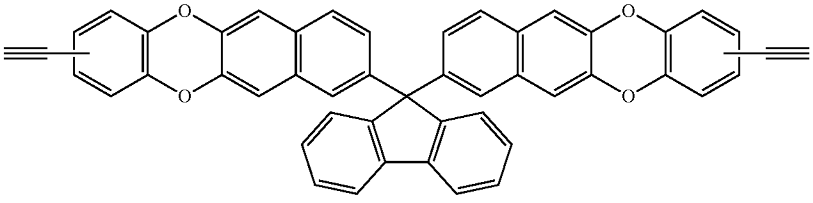

-continued (1H)

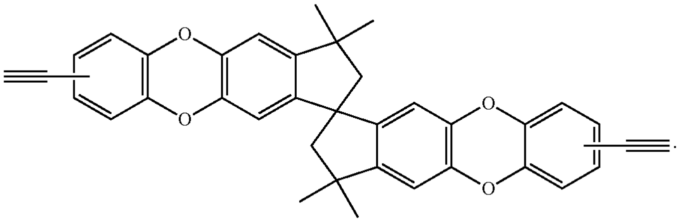

3. The material for forming an organic film according to claim 1, wherein the component (A) satisfies 1.00≤Mw/Mn≤1.10, where Mw is a weight-average molecular weight and Mn is a number-average molecular weight measured by gel permeation chromatography in terms of polystyrene.

4. The material for forming an organic film according to claim 1, wherein the component (B) is a mixture of one or more kinds of organic solvent having a boiling point of lower than 180° C. and one or more kinds of organic solvent having a boiling point of 180° C. or higher.

5. The material for forming an organic film according to claim 1, further comprising at least one of (C) an acid generator, (D) a surfactant, (E) a crosslinking agent, and (F) a plasticizer.

6. A substrate for manufacturing a semiconductor device, comprising an organic film on the substrate, the organic film being a cured film of the material for forming an organic film according to claim 1.

7. A method for forming an organic film employed in a semiconductor device manufacturing process, the method comprising:

spin-coating a substrate to be processed with the material for forming an organic film according to claim 1; and heating the substrate to be processed coated with the material for forming an organic film under an inert gas atmosphere at a temperature of 50° C. or higher to 600° C. or lower for 10 seconds to 7200 seconds to obtain a cured film.

8. A method for forming an organic film employed in a semiconductor device manufacturing process, the method comprising:

spin-coating a substrate to be processed with the material for forming an organic film according to claim 1;

heating the substrate to be processed coated with the material for forming an organic film in air at a temperature of 50° C. or higher to 300° C. or lower for 5 seconds to 600 seconds to form a coating film; and then performing a heat treatment under an inert gas atmosphere at a temperature of 200° C. or higher to 600° C. or lower for 10 seconds to 7200 seconds to obtain a cured film.

9. The method for forming an organic film according to claim 7, wherein the inert gas has an oxygen concentration of 1% or less.

10. The method for forming an organic film according to claim 8, wherein the inert gas has an oxygen concentration of 1% or less.

11. The method for forming an organic film according to claim 7, wherein the substrate to be processed has a structure or a step with a height of 30 nm or more.

12. The method for forming an organic film according to claim 8, wherein the substrate to be processed has a structure or a step with a height of 30 nm or more.

13. A patterning process comprising:

forming an organic film by using the material for forming an organic film according to claim 1 on a substrate to be processed;

forming a silicon-containing resist middle layer film by using a silicon-containing resist middle layer film material on the organic film;

forming a resist upper layer film by using a photoresist composition on the silicon-containing resist middle layer film;

forming a circuit pattern in the resist upper layer film;

transferring the pattern to the silicon-containing resist middle layer film by etching while using the resist upper layer film having the formed pattern as a mask;

transferring the pattern to the organic film by etching while using the silicon-containing resist middle layer film having the transferred pattern as a mask; and further transferring the pattern to the substrate to be processed by etching while using the organic film having the transferred pattern as a mask.

14. A patterning process comprising:

forming an organic film by using the material for forming an organic film according to claim 1 on a substrate to be processed;

forming a silicon-containing resist middle layer film by using a silicon-containing resist middle layer film material on the organic film;

forming an organic antireflective coating on the silicon-containing resist middle layer film;

forming a resist upper layer film by using a photoresist composition on the organic antireflective coating, so that a 4-layered film structure is constructed;

forming a circuit pattern in the resist upper layer film;

transferring the pattern to the organic antireflective coating and the silicon-containing resist middle layer film by etching while using the resist upper layer film having the formed pattern as a mask;

transferring the pattern to the organic film by etching while using the silicon-containing resist middle layer film having the transferred pattern as a mask; and further transferring the pattern to the substrate to be processed by etching while using the organic film having the transferred pattern as a mask.

15. A patterning process comprising:

forming an organic film by using the material for forming an organic film according to claim 1 on a substrate to be processed;

forming an inorganic hard mask selected from a silicon oxide film, a silicon nitride film, a silicon oxynitride film, a titanium oxide film, and a titanium nitride film on the organic film;

forming a resist upper layer film by using a photoresist composition on the inorganic hard mask;

forming a circuit pattern in the resist upper layer film;

transferring the pattern to the inorganic hard mask by etching while using the resist upper layer film having the formed pattern as a mask;

transferring the pattern to the organic film by etching while using the inorganic hard mask having the transferred pattern as a mask; and further transferring the pattern to the substrate to be processed by etching while using the organic film having the transferred pattern as a mask.

16. A patterning process comprising:

forming an organic film by using the material for forming an organic film according to claim 1 on a substrate to be processed;

forming an inorganic hard mask selected from a silicon oxide film, a silicon nitride film, a silicon oxynitride film, a titanium oxide film, and a titanium nitride film on the organic film;

forming an organic antireflective coating on the inorganic hard mask;

forming a resist upper layer film by using a photoresist composition on the organic antireflective coating, so that a 4-layered film structure is constructed;

forming a circuit pattern in the resist upper layer film;

transferring the pattern to the organic antireflective coating and the inorganic hard mask by etching while using the resist upper layer film having the formed pattern as a mask;

transferring the pattern to the organic film by etching while using the inorganic hard mask having the transferred pattern as a mask; and further transferring the pattern to the substrate to be processed by etching while using the organic film having the transferred pattern as a mask.

17. The patterning process according to claim 16, wherein the inorganic hard mask is formed by a CVD method or an ALD method.

18. The patterning process according to claim 16, wherein the circuit pattern is formed by a lithography using light with a wavelength of 10 nm or more to 300 nm or less, a direct drawing with electron beam, nanoimprinting, or a combination thereof.

19. The patterning process according to claim 16, wherein when the circuit pattern is formed, the circuit pattern is developed by alkali development or with an organic solvent.

20. The patterning process according to claim 16, wherein the substrate to be processed is a semiconductor device substrate or the semiconductor device substrate coated with any of a metal film, a metal carbide film, a metal oxide film, a metal nitride film, a metal oxycarbide film, and a metal oxynitride film.

21. The patterning process according to claim 20, wherein the metal comprises silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

22. A compound for forming an organic film shown by the following general formula (1C), (1D), or (1E), (1C)

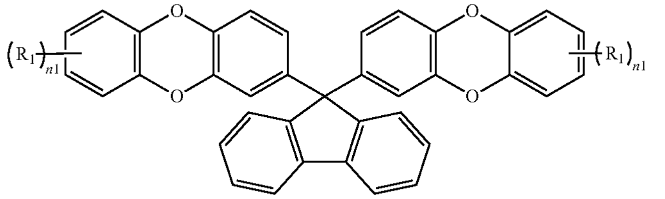

(1D)

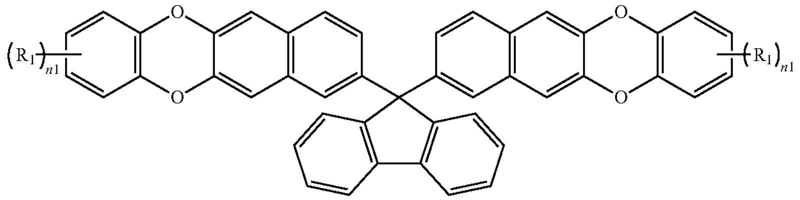

(1E)

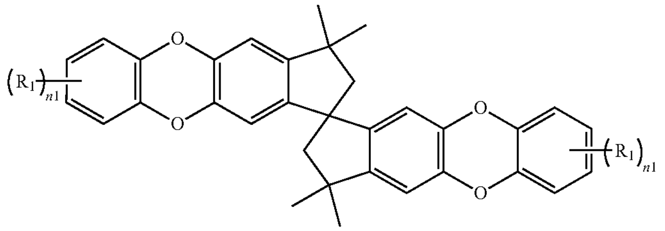

wherein n1 represents an integer of 1 or 2, and a hydrogen atom of a benzene ring in the formula (1C), (1D), or (1E) is optionally substituted with a fluorine atom,

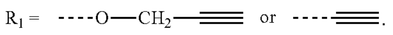

23. The compound for forming an organic film according to claim 22, wherein the compound for forming an organic film is shown by the following formula (1F), (1G), or (1H),
(1F)
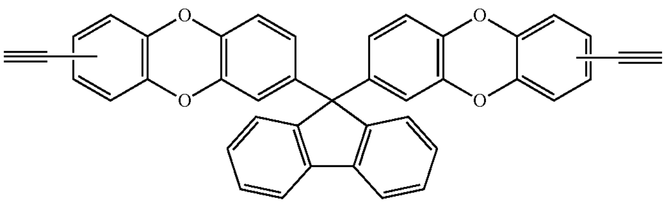
(1G)
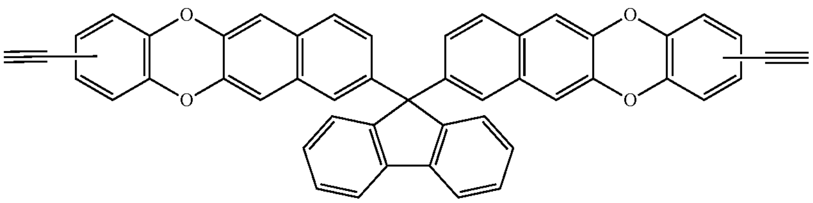
(1H)
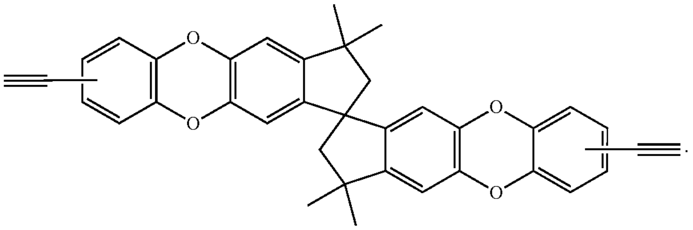
* * * * *